(12) United States Patent
MacLeod

(10) Patent No.: US 6,784,163 B1
(45) Date of Patent: Aug. 31, 2004

(54) INHIBITION OF CATIONIC AMINO ACID TRANSPORTER PROTEIN AND USES THEREOF

(76) Inventor: Carol L. MacLeod, 3770 Wellborn St., San Diego, CA (US) 93103

( * ) Notice: Subject to any disclaimer, the term of this patent is extended or adjusted under 35 U.S.C. 154(b) by 1389 days.

(21) Appl. No.: 09/238,972

(22) Filed: Jan. 27, 1999

Related U.S. Application Data

(63) Continuation-in-part of application No. 08/187,634, filed on Jan. 26, 1994, now Pat. No. 5,866,123, which is a continuation-in-part of application No. 07/686,322, filed on Apr. 11, 1991, now Pat. No. 5,312,733, which is a continuation-in-part of application No. 07/509,684, filed on Apr. 13, 1990, now abandoned.

(51) Int. Cl.[7] ......................... A01N 43/04; A61K 31/70
(52) U.S. Cl. ............................. 514/44; 435/6; 435/325; 435/375; 536/23.1; 536/24.5
(58) Field of Search ................................ 514/44; 435/6, 435/325, 375, 911, 366; 536/23.1, 24.5, 24.31

(56) References Cited

U.S. PATENT DOCUMENTS 5,312,733 A  *  5/1994  MacLeod ................... 435/69.1
5,585,479 A  *  12/1996  Hoke et al. ................. 536/24.5

OTHER PUBLICATIONS

Rojanasakul et al., Antisense oligonucleotidde therapeutics: drug delivery and targeting, Advanced Drug Delivery Reviews, vol. 18, pp. 115–131, 1996.*
Gewirtz et al., Facilitating oligonucleotide delivery: helping antisense deliver on its promise, Proc. Natl. Acad. Sci., vol. 93, pp. 3161–6163, Apr. 1996.*
Branch, A good antisense molecule is hard to find, TIBS, vol. 23, pp. 45–50, Feb. 1998.*

* cited by examiner

Primary Examiner—Sean McGarry
Assistant Examiner—James Douglas Schultz
(74) Attorney, Agent, or Firm—Benjamin Aaron Adler

(57) ABSTRACT

The present invention provides methods of inhibiting cationic amino acid transport by means of antisense and antibody technology specific for the CAT2 transporter. Further, the present invention provides methods of treating a disease characterized by undesirable levels of nitric oxide.

11 Claims, 26 Drawing Sheets

Factor VIII                    CD31 (PCAM)

Sstl digest
ES cell genomic DNA

Kpnl digest

Sstl digest
Mouse genomic DNA

SEQUENCE LISTING

<160> NUMBER OF SEQ ID NOS: 16

<210> SEQ ID NO 1
<211> LENGTH: 25
<212> TYPE: DNA
<213> ORGANISM: artificial sequence
<220> FEATURE:
<222> LOCATION: 489..515
<223> OTHER INFORMATION: CAT2 sense oligonucleotide

<400> SEQUENCE: 1
tatccaagac ttctttgccg tgtgc                                              25

<210> SEQ ID NO 2
<211> LENGTH: 23
<212> TYPE: DNA
<213> ORGANISM: artificial sequence
<220> FEATURE:
<222> LOCATION: 1406..1429
<223> OTHER INFORMATION: CAT2 antisense oligonucleotide

<400> SEQUENCE: 2
gtaggctgaa accctgtcct tgc                                                23

<210> SEQ ID NO 3
<211> LENGTH: 27
<212> TYPE: DNA
<213> ORGANISM: artificial sequence
<220> FEATURE:
<221> NAME/KEY: primer_bind
<222> LOCATION: 1453..1470
<223> OTHER INFORMATION: Primer used in RT of total RNA from mouse cell
      lines SL12.4 and J774, mouse liver and skeletal
      muscle tissues, and from unstimulated and
      stimulated splenocytes to detect CAT2 promoter usage.

<400> SEQUENCE: 3
cgcgaattcc gactgtcgtg tgggcag                                            27

<210> SEQ ID NO 4
<211> LENGTH: 24
<212> TYPE: DNA
<213> ORGANISM: artificial sequence
<220> FEATURE:
<221> NAME/KEY: primer_bind
<222> LOCATION: 489..513
<223> OTHER INFORMATION: Primer used to amplify Cat2 isoform

<400> SEQUENCE: 4
tatccagact tctttgccgt gtgc                                               24

<210> SEQ ID NO 5
<211> LENGTH: 23
<212> TYPE: DNA
<213> ORGANISM: artificial sequence
<220> FEATURE:
<221> NAME/KEY: primer_bind
<222> LOCATION: 1406..1429
<223> OTHER INFORMATION: Primer used to amplify Cat2a isoform

<400> SEQUENCE: 5
gtaggctgaa accctgtcct tgc                                                23

<210> SEQ ID NO 6
<211> LENGTH: 22
<212> TYPE: DNA

```
<213> ORGANISM: artificial sequence
<220> FEATURE:
<222> LOCATION: 1071..1093
<223> OTHER INFORMATION: CAT2 specific 5(-end labeled oligonucleotide
      probe used to authenticate PCR product

<400> SEQUENCE: 6
tcccaatgcc tcgtgtaatc ta                                             22

<210> SEQ ID NO 7
<211> LENGTH: 22
<212> TYPE: DNA
<213> ORGANISM: artificial sequence
<220> FEATURE:
<222> LOCATION: 1159..1181
<223> OTHER INFORMATION: CAT2a specific 5(-end labeled oligonucleotide
      probe used to authenticate PCR product

<400> SEQUENCE: 7
tgcagtcatc gtggcagcaa cg                                             22

<210> SEQ ID NO 8
<211> LENGTH: 22
<212> TYPE: DNA
<213> ORGANISM: artificial sequence
<220> FEATURE:
<221> NAME/KEY: primer_bind
<223> OTHER INFORMATION: Oligonucleotide used to amplify Cat2
      transcripts from the liver of Cat2-/- mice

<400> SEQUENCE: 8
tgtctgcgcg gatctggaaa gg                                             22

<210> SEQ ID NO 9
<211> LENGTH: 22
<212> TYPE: DNA
<213> ORGANISM: artificial sequence
<220> FEATURE:
<221> NAME/KEY: primer_bind
<223> OTHER INFORMATION: Oligonucleotide used to amplify Cat2
      transcripts from the liver of Cat2-/- mice

<400> SEQUENCE: 9
gccctgaatg aactgcagga cg                                             22

<210> SEQ ID NO 10
<211> LENGTH: 27
<212> TYPE: DNA
<213> ORGANISM: artificial sequence
<220> FEATURE:
<221> NAME/KEY: primer_bind
<223> OTHER INFORMATION: Oligonucleotide used to amplify Cat2
      transcripts from the liver of Cat2-/- mice

<400> SEQUENCE: 10
cgcgaattcg tctggatact ctgccag                                        27

<210> SEQ ID NO 11
<211> LENGTH: 23
<212> TYPE: DNA
<213> ORGANISM: artificial sequence
<220> FEATURE:
<221> NAME/KEY: primer_bind
<223> OTHER INFORMATION: Primer used to clone the NOS2 cDNA by RT/PCR
      from mouse mammary tumor cDNA

<400> SEQUENCE: 11
cagtgccctg ctttgtgcga agt                                            23
```

```
<210> SEQ ID NO 12
<211> LENGTH: 25
<212> TYPE: DNA
<213> ORGANISM: artificial sequence
<220> FEATURE:
<221> NAME/KEY: primer_bind
<223> OTHER INFORMATION: Primer used to clone the NOS2 cDNA by RT/PCR
      from mouse mammary tumor cDNA

<400> SEQUENCE: 12
aacgtttctg gctcttgagc tggaa                                          25

<210> SEQ ID NO 13
<211> LENGTH: 67
<212> TYPE: DNA
<213> ORGANISM: artificial sequence
<220> FEATURE:
<223> OTHER INFORMATION: Nucleotide sequence of truncated Cat2 cDNA from
      Cat2-/- liver

<400> SEQUENCE: 13
ggcactgccc cagtacgtcc agtgtcgcaa gagcatggag tggcaccttt gacgaacttc    60
ttaataa                                                              67

<210> SEQ ID NO 14
<211> LENGTH: 5
<212> TYPE: PRT
<213> ORGANISM: artificial sequence
<220> FEATURE:
<223> OTHER INFORMATION: Predicted protein sequence coded by truncated
      Cat2 cDNA

<400> SEQUENCE: 14

Met Glu Trp His Leu
              5

<210> SEQ ID NO 15
<211> LENGTH: 21
<212> TYPE: DNA
<213> ORGANISM: artificial sequence
<220> FEATURE:
<223> OTHER INFORMATION: Nucleotide sequence of the Neomycin (Neo)
      cassette

<400> SEQUENCE: 15
ttcttctgag gggatttcca g                                              21

<210> SEQ ID NO 16
<211> LENGTH: 9
<212> TYPE: DNA
<213> ORGANISM: artificial sequence
<220> FEATURE:
<223> OTHER INFORMATION: Nucleotide sequence of Exon 3 at point where
      Neo cassette is spliced

<400> SEQUENCE: 16 gtacgtcca                                                             9
```

INHIBITION OF CATIONIC AMINO ACID TRANSPORTER PROTEIN AND USES THEREOF

CROSS-REFERENCE TO RELATED APPLICATION

This continuation-in-part patent application claims benefit of continuation-in-part application U.S. Ser. No. 08/187,634, filed Jan. 26, 1994 now U.S. Pat. No. 5,866,123, which claims benefit of continuation-in-part application U.S. Ser. No. 07/686,322, filed Apr. 11, 1991, now U.S. Pat. No. 5,312,733, which claims benefit of continuation-in-part application U.S. Ser. No. 07/509,684, filed Apr. 13, 1990, now abandoned.

BACKGROUND OF THE INVENTION

1. Field of the Invention

The present invention relates generally to cellular biochemistry and molecular biology of cationic amino acid transporter proteins. More particularly, the present invention relates to uses for a cationic amino acid transporter protein.

2. Description of the Related Art

Cationic amino acids such as arginine are important in mammalian cellular and tissue function. Biochemically distinct systems mediate their transport into and out of cells; two families of cloned mammalian cationic amino acid transporters have been reported.

Apart from protein synthesis, the cationic amino acid arginine has other crucial roles in cellular processes. Arginine and its transport are essential for the regulated production of nitric oxide (NO). Nitric oxide synthesis requires transport of external arginine into such cells as macrophages, cardiac myocytes, vascular smooth muscle cells and astrocytes. Arginine is the sole precursor for the synthesis of nitric oxide as the amino group donor for nitric oxide, a reaction catalyzed by a family of nitric oxide synthases (NOS). The enzymes nNOS (neural NOS) and eNOS (endothelial NOS) are constitutively expressed in brain and endothelial cells. They transiently produce small amounts of nitric oxide regulated by $Ca^{2+}$ flux. Inducible NOS (iNOS) is expressed in response to specific cellular signals and produces large amounts of NOS over a sustained period of several days. iNOS activity is rate limited by L-arginine transport. In contrast, nNOS and eNOS activity is independent of L-arginine transport.

On a physiological level, nitric oxide is the most potent vasodilator known and is required for a variety of cellular functions. For example, the cytotoxic activity of macrophages is dependent on nitric oxide. The production of nitric oxide in the vascular endothelium regulates blood pressure, and nitric oxide is a neurotransmitter. Nitric oxide has beneficial biological functions that serve a variety of physiological processes, however, nitric oxide also has less salutary effects. Nitric oxide is unstable and it inhibits enzymes. Intracellular nitric oxide is a highly reactive free radical that reacts with other free radicals, molecular oxygen and heavy metals. Persistent high concentrations of nitric oxide can cause DNA damage.

The role of nitric oxide in pathophysiology is thus suggested, but its precise dimensions are not clear. Although nitric oxide might in some way modulate tumor development, it has been unclear whether it inhibits or stimulates tumor growth, angiogenesis or metastasis.

With respect to the role of nitric oxide in cancer, in particular breast cancer, it has been observed that breast cancer cell lines, human breast cancer cells and mouse mammary tumor cell lines produce nitric oxide in amounts that correlate with tumor grade. Breast cancer tissue samples have been shown to express iNOS in the infiltrating macrophages of the tumor. It has been shown recently that S-nitroso-N-acetyl-DL-penicillamine [a nitric oxide-releasing compound] changes the conformation of recombinant wild-type murine p53 protein and the behavior of p53 protein in CF7 human breast cancer cells. Recent work has shown that p53 expression down-regulates iNOS expression. Additionally, nitric oxide directly affects the regulation of p53 gene expression as well as the conformation and activity of the p53 protein. It is possible that nitric oxide induces mutations in p53 that abrogate iNOS regulation, and nitric oxide induced mutations in p53 could contribute to cell transformation. Data suggests that excess nitric oxide produced in inflamed tissues might play a role in carcinogenesis by impairing the tumor suppressor function of p53.

Further, the role of nitric oxide in angiogenesis has great relevance to breast cancer and vascular density measurement is now widely recognized as a prognostic indicator in breast cancer. In the early 90s, reports began to associate the production of nitric oxide with angiogenesis. Since then, there have been a large series of conflicting reports indicating that nitric oxide stimulates or inhibits angiogenesis. Recently, it has been established that hypoxia, such as that found in early tumors, induces vascular endothelial growth factor (VEGF), angiogenesis and iNOS. Further, very recent work has clearly established that nitric oxide is required for vascular endothelial growth factor to mediate angiogenesis in vitro.

To further elucidate the biochemical underpinnings of nitric oxide synthesis, the identification of cationic amino acid transporter cDNAs was an important first step. The role of regulated transport in the functioning of cell types such as macrophages and others can thus be better understood and manipulated. The majority of arginine transport in most cells and tissues is mediated by a transport system apparently encoded by three genes: Cat1, Cat2 and Cat3. Cat1 and Cat2 genes encode similar proteins, CAT1 and CAT2 (e.g. MacLeod, C. L., *Biochem. Soc. Trans.*, 24:846–852 (1996)), comprising a functionally defined, transport system ($y^+$), which facilitates the transport of the cationic amino acids lysine, arginine and ornithine in a sodium-independent manner. The Cat2 gene encodes two protein isoforms, CAT2 and CAT2a, results of mutually exclusive alternate splicing. The CAT2a protein exhibits a significantly lower (10-fold) apparent affinity for its substrate than either CAT1 or CAT2.

The various CAT transcripts are expressed in distinct patterns. CAT1 transcripts are constitutively and nearly ubiquitously expressed in normal tissues and cell lines. The adult liver does not express CAT1, but exclusively expresses the CAT2a isoform. The expression of CAT2 and CAT2a is much more limited than that of CAT1. Transcripts are abundant only in liver, skeletal muscle, and stomach as well as activated macrophages. Both Cat1 and Cat2 genes are inducible in a variety of circumstances. Expression of the newly reported Cat3 gene is limited to the brain.

With respect to the role of CATs in immune function, resting splenocytes (largely comprised of quiescent T- and B-cells) express predominantly CAT1 mRNA, yet exhibit extremely limited L-arginine and L-lysine transport. Following mitogen or antigen mediated T-cell activation, however, extracellular L-arginine is needed and both CAT1 and CAT2 transcripts rapidly accumulate.

Similarly, quiescent macrophages express only CAT1 mRNA, which steadily decreases for 24 hours following activation. In contrast, CAT2 expression is undetectable until activation. Following activation with lipopolysaccharide (LPS) and IFN-γ, macrophages increase system y+ transport following activation to provide these cells with adequate L-arginine for nitric oxide synthesis. At the same time, iNOS is induced. Such observations reflect macrophage requirements for extracellular L-arginine transport for nitric oxide synthesis via the inducible form of nitric oxide synthase (iNOS). It would thus appear that in activated macrophages, CAT2 mediated arginine transport regulates the arginine:nitric oxide pathway.

Although the functions of the CAT genes may be seen as overlapping, they are responsive to different cellular signals. Cat2 gene expression is inducible and highly tissue-specific, while Cat1 is widely expressed and believed to be a housekeeping gene. CAT1 knockout mice are not viable, are runted, anemic and die within hours of birth. CAT2, but not CAT1, mRNA is induced in response to specific cellular activators in several cultured cell systems and in vivo. For example, in macrophages and in mammary cell lines an induction of CAT2 mRNA is seen in response to LPS and IFN-γ coordinately with iNOS. CAT1 mRNA levels decrease or remain low and unaltered. The co-induction of CAT2 and iNOS has been observed in such cell types as macrophages, vascular smooth muscle cells, astrocytes and other glial cells, liver and numerous others.

The prior art lacks effective and specific mechanisms to precisely inhibit cationic amino acid transport in specific cell or tissue types and thereby curtail nitric oxide production in these cells or tissues. The present invention fulfills this long-standing need and desire in the art.

SUMMARY OF THE INVENTION

The identification and manipulation of the precise L-arginine transporter involved in nitric oxide production provides new opportunities for therapeutic intervention. The instant invention delineates CAT2 involvement in L-arginine transport and nitric oxide synthesis in various cell types and pathological conditions. It further provides novel and powerfully precise means to regulate this important substance. The instant invention strongly demonstrates a stimulatory role for nitric oxide in tumor growth. Data from studies using transgenic mice with an iNos$^{-/-}$ genotype demonstrate that lack of iNOS inhibits tumor formation.

One object of the present invention is to provide an antisense methodology for inhibiting cationic amino acid transport comprising the step of administering to a human or a non-human mammal an effective dose of the antisense oligonucleotides of the present invention. Thus, the present invention provides an antisense oligonucleotide directed against CAT2 mRNA. A representative antisense oligonucleotide has the nucleotide sequence: GTAGGCTGAAAC-CCTGTCCTTGC (SEQ ID No. 2). Further, the present invention provides a pharmaceutical composition comprising the antisense oligonucleotide directed against CAT2 mRNA and a physiologically acceptable carrier.

In another embodiment of the present invention, there is provided a method of treating breast cancer in an individual in need of such treatment, comprising the step of administering to said individual an effective dose of the antisense oligonucleotide directed against CAT2 mRNA.

In another embodiment of the present invention, there is provided a method of treating breast cancer in an individual in need of such treatment, comprising the step of administering to said individual an effective dose of anti-CAT2 antibody.

In one embodiment of the present invention, there is provided a method of treating a pathophysiological state in a human or a non-human mammal, wherein said state is characterized by production of an undesirable level of nitric oxide, comprising the step of administering an effective dose of the antisense oligonucleotides or antibody of the present invention.

In another embodiment of the present invention, there is provided a method of treating a pathophysiological state in a mammal, wherein said state is characterized by production of an undesirable level of nitric oxide, comprising the step of administering an effective dose of a substance designed to specifically block the capacity of CAT2 cell surface protein to transport arginine such as an anti-CAT2 antibody to block cationic amino acid transport and concomitant nitric oxide synthesis. This can be accomplished by using cell lines from a CAT2 deficient and wild type mice to screen for substances that block transport.

In yet another embodiment of the present invention, there is provided a transgenic animal lacking exon 2 of the CAT2 gene and lacking any function of the CAT2 gene.

In another embodiment of the present invention, there is provided a cell line derived from the transgenic animal disclosed herein.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 10 shows CAT mRNA in skeletal muscle following hepatectomy, splenectomy and fasting.

FIG. 17 characterizes the established cell lines from the mTag mammary tumor.

FIG. 22 depicts the targeted disruption of Cat2.

FIG. 23 is a schematic illustration of the CAT2/2a protein. The 14 transmembrane domain model is shown with the bold line indicating the region of CAT2 that was deleted by ablating Exon 2. The arrow points to the approximate position of a highly conserved glutamic acid at position 109 in the $3^{rd}$ transmembrane domain. The dotted line indicates the region that differs between CAT2 and CAT2a.

FIG. 24 shows Cat gene expression.

FIG. 25 shows the functional analysis of $Cat2^{-/-}$ peritoneal macrophages.

DETAILED DESCRIPTION OF THE INVENTION

Figure 1A:
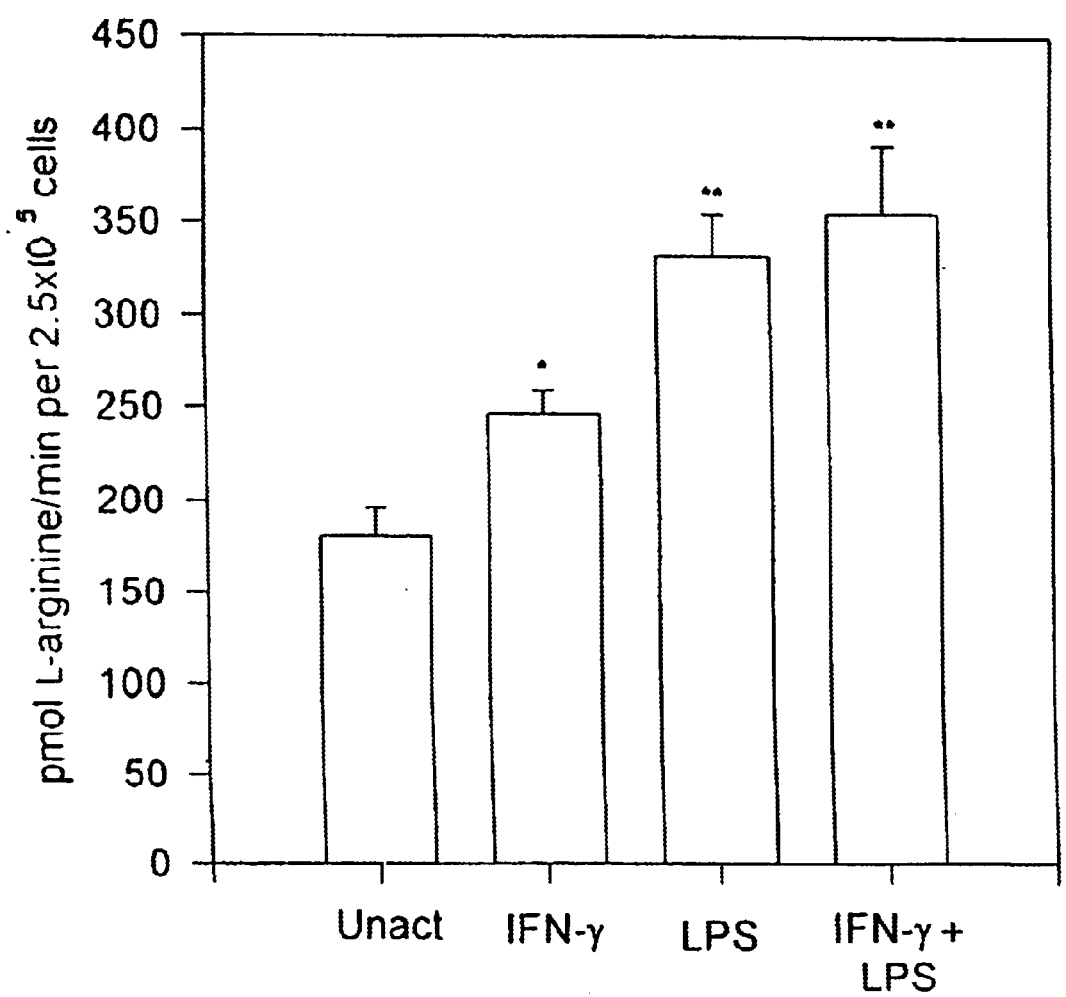
FIG. 1A demonstrates L-arginine and L-leucine transport in J774 macrophages. Induction of [$^3$H]L-arginine transport was seen following treatment with IFN-γ, LPS, or IFN-γ and LPS. Macrophages were either untreated (Unact), treated with IFN-γ (20 units/ml) for 19 hours (IFN-γ), or with LPS (100 ng/ml) for 17 hours(LPS), or in combination of 2 hr IFN-γ treatment followed by 17 hr LPS (IFN-γ and LPS). [$^3$H]L-arginine uptake was performed in the presence of sodium, and data shown represent the mean±SEM of three independent experiments. *p<0.01, **p<0.001.

The present invention describes how novel antisense oligonucleotides can be employed to prevent cationic amino acid transport, which in turn blocks production of nitric oxide in cells such as activated macrophages or cancer cells. The present invention provides these novel antisense oligonucleotides to be used in therapy. The novel antisense oligonucleotides may comprise determinant of any length, most preferably around 24 bases. Thus, the present invention makes available novel antisense oligonucleotides for use in gene therapy where it may be desirable to inhibit production of nitric oxide.

The methods of the present invention may be applied to any animal. Most preferably, the novel compositions useful in the methods of the present invention are administered to a human. Many tissue or cell targets are suggested for this invention, the most prominent being macrophages, tumor cells, or astrocytes.

Generally, the dose of the novel antisense oligonucleotides useful in the methods of the present invention is any that inhibits the production of nitric oxide in the animal. A person having ordinary skill in the art of gene therapy would readily be able to determine an appropriate dose of the novel antisense oligonucleotides of the instant invention.

Generally, the methods of treating a pathophysiological state of the present invention may be useful for any disease characterized by an undesirable level of nitric oxide production. Preferably, this method will treat diseases selected from the group consisting of sepsis, cachexia, neoplastic diseases such as Kaposi's sarcoma, cerebral malaria, capillary leak syndrome and autoimmune disease. Representative autoimmune diseases include systemic lupus erythematosus, rheumatoid arthritis and multiple sclerosis. Representative neoplastic diseases include breast and lung cancer.

The dosage administered in the methods of the present invention is dependent upon the age, weight, kind of concurrent treatment, if any, and nature of the pathophysiological state. The effective composition useful in the methods of the present invention may be employed in such forms as liposomes or various viral vectors.

The present invention also provides a method of inhibiting cationic amino acid transport including arginine by administering to a human or a non-human animal an effective dose of novel antisense oligonucleotides.

The present invention is additionally directed to the use of an anti-CAT2 antibody to inhibit nitric oxide production. The present invention describes how this antibody can be employed to prevent cationic amino acid transport, which in turn blocks production of nitric oxide in cells such as activated macrophages or cancer cells. Thus, the present invention makes available an antibody against CAT2 and a method of using this antibody where it may be desirable to inhibit production of nitric oxide.

Finally, the present invention is directed to a transgenic animal and cell lines derived therefrom. A transgenic animal and cell lines derived from such animals would be useful for the development of further pharmaceutical strategies to block transport.

The following examples are given for the purpose of illustrating various embodiments of the invention and are not meant to limit the present invention in any fashion:

EXAMPLE 1

Cell Culture

The mouse macrophage-like cell line J774 and bone marrow-derived macrophages (BMMs) were cultured using standard tissue culturing techniques in RPMI 1640 supplemented with 10% serum supreme (BioWhittaker), L-glutamine (2 mM) and penicillin/streptomycin (100 units/ml; 100 μg/ml; Life Technologies) on bacterial petri dishes. BMMs were produced from femoral marrow cells of mice and cultured for six days, supplemented with recombinant human CSF-1 (10,000 units/ml). RPMI 1640 select-amine kit (Life Tech) was used for nitrite assays lacking L-arginine.

EXAMPLE 2

[$^3$H]-arginine Uptake

Macrophages were cultured as described above and replated in 24-well plates (2.5×10$^5$ cells/well) in 1.0 ml supplemented RPMI 1640. Following a two hour attachment period, cells were primed with mouse IFN-γ (20 units/ml; Sigma) for two hours, then treated with bacterial LPS from E. coli 055:B5 (100 ng/ml; Sigma) for 17 hours.

Radiolabeled uptake was performed on cells incubated in 0.5 ml for two minutes at 37° C. with uptake solution (137 mM NaCl, 5.4 mM KCl, 2.8 mM CaCl$_2$, 1.2 mM MgSO$_4$, 10 mM HEPES/Tris, pH 7.4; Na$^+$-free solution substituted NaCl with equimolar N-methyl-D-glucamine) supplemented with either 0.1 mM L-arginine containing 1.0 μCi/ml L-[$^3$H]-arginine or 0.1 mM leucine containing 1.0 μCi/ml L-[$^3$H]-leucine.

The uptake reaction was stopped by adding ice cold stop solution (137 mM NaCl and 14 mM Tris/HCl, pH 7.4). Background labeling was controlled with uptakes at 0° C. Specificity of transport was ensured by adding 5.0 mM of the indicated L-amino acids or L-NMMA and L-NNA in the uptake solution. The cells were lysed in 0.5 ml of 0.5% Triton X-100. Two 150 μl samples were removed per well and the radioactivity determined by liquid scintillation.

L-arginine transport was significantly induced by IFN-γ (p<0.01) alone, with greatest induction by LPS (p<0.001) alone or in combination with IFN-γ (p<0.001). There was no significant difference in L-arginine transport in cells treated with IFN-γ or IFN-γ and LPS, suggesting LPS alone was sufficient to induce maximal L-arginine transport in J774 cells.

Figure 1B:
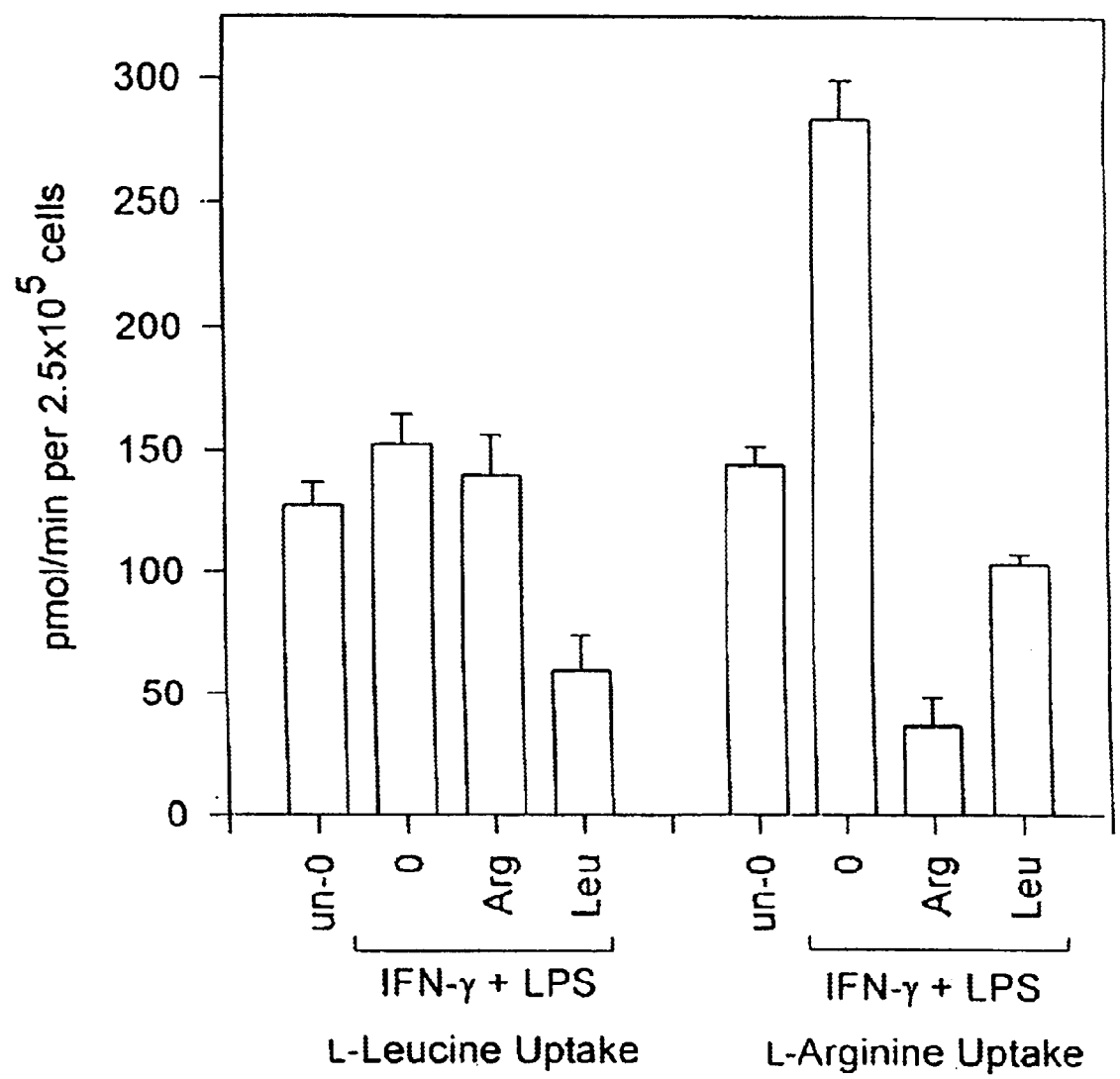
FIG. 1B shows [$^3$H]L-arginine and [$^3$H]L-leucine transport in J774 inactivated and activated macrophages. The uptake was performed with inactivated macrophages (un) or activated macrophages (IFN-γ and LPS) which were treated with IFN-γ (20 units/ml) followed by LPS (100 ng/ml, 17 hrs), in the presence of sodium with either no inhibitor (0), or in the presence of L-arginine (Arg), or L-leucine (Leu), each at 5.0 mM concentration. Graph represents mean±SEM of four independent experiments.

The combined IFN-γ and LPS induction of L-arginine transport was inhibited by L-arginine and L-leucine (in the presence of sodium, Na+; FIG. 1B). L-leucine transport, which was not induced in activated macrophages, was only inhibited by L-leucine but not L-arginine (FIG. 1B). Significant inhibition of L-arginine transport by L-leucine and L-homoserine was observed in the presence of Na+ (p<0.001) in IFN-γ and LPS activated macrophages (FIG. 2A), with no significant inhibition with L-aspartic acid or L-NNA.

Figure 2:
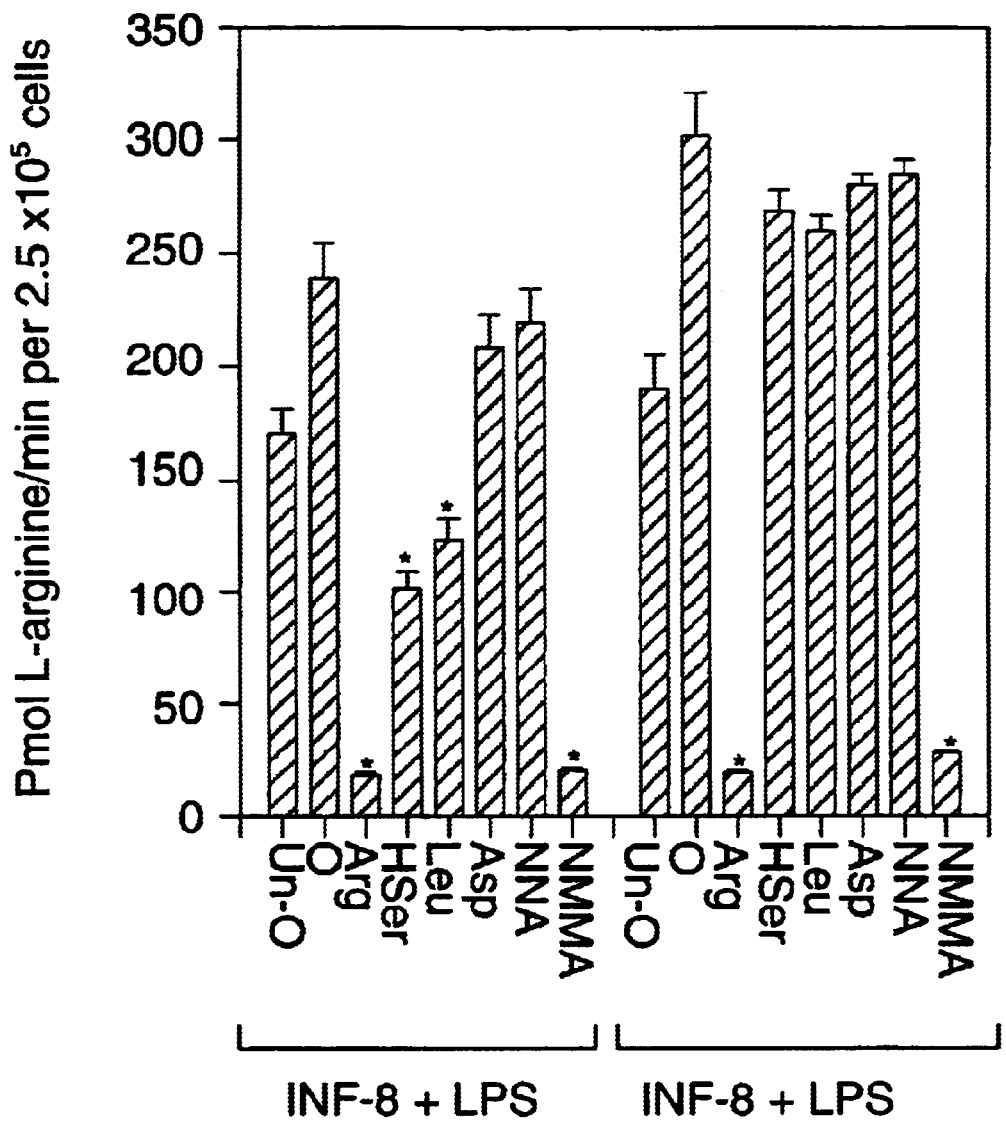
FIG. 2 is a characterization of [$^3$H]L-arginine transport in J774 cells. [$^3$H]L-arginine uptake was performed with inactivated macrophages (Un) or activated (IFN-γ and LPS) J774 which were treated with IFN-γ (20 units/ml, 2 hours) followed by LPS (100 ng/ml, 17 hrs), in the absence of sodium, using N-Methyl-D-glucamine (Left), with either no inhibitor (0), or in the presence of L-arginine (Arg), L-homoserine (Hser), L-leucine (Leu), L-aspartic acid (Asp), L-N$^G$-nitro-arginine (NNA, a dipolar NOS inhibitor), or L-N$^G$-methyl-arginine (NMMA, a system y+ mediated NOS inhibitor), each at 5.0 mM concentration. Data represents the mean±SEM of three independent experiments for J774 cells (A, *p<0.001).

The system y+ mediated NOS inhibitor, L-NMMA, significantly inhibited L-arginine transport without the requirement for Na+ (p<0.01, FIG. 2). System y+ transport was also observed in IFN-γ and LPS activated BMMs, with L-homoserine and L-leucine inhibiting L-arginine transport only in the presence of Na+. There was no significant inhibition by L-aspartic acid. This increase in L-arginine transport seen in activated macrophages, is also observed in astrocytes treated with IFN-γ and LPS.

EXAMPLE 3
Nitrite Assay

Macrophages were plated onto 96-well plates ($4 \times 10^4$ cells/well) in 0.2 ml RPMI 1640 media. Nitrite levels were determined from triplicate cell-culture supernatants using equal volumes of Griess reagent (1% sulfanilamide, 0.1% N-(1-naphthyl)ethylenediamine dihydrochloride, 2.1% phosphoric acid). macrophages were treated with IFN-γ (20 units/ml) for 2 hours, followed by LPS (100 ng/ml) for 17 hours. Fresh media was applied for 24 hours, and 100 μl supernatant samples were collected. Absorbance was read at 543 nm on 96-well plates and sodium nitrite (1–50 μm) used as a standard.

Nitrite levels were also measured in Xenopus oocytes injected with mRNA from activated and inactivated J774 cells. The oocyte nitrite assay was performed 2–3 days post mRNA injection, with six oocytes per well in 96-well plates and measured at 543 nm in triplicate, as described above.

Figure 3A:
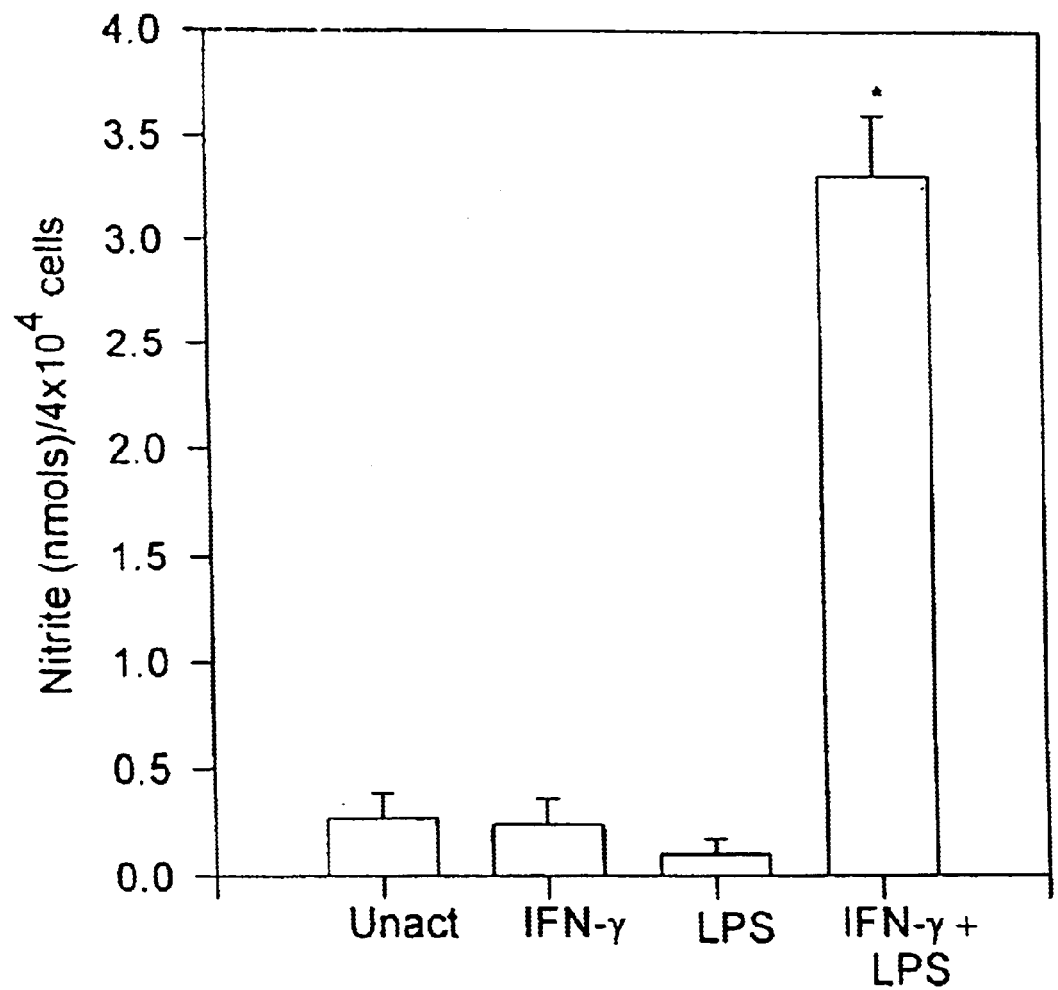
FIG. 3A demonstrates nitric oxide synthesis in J774 macrophages by measuring nitrite production in resting and activated J774 cells. Macrophages were either untreated (Unact), treated with IFN-γ (20 units/ml) for 2 hours (IFN-γ) or with LPS (100 ng/ml) for 17 hours (LPS) or in combination of 2 hours IFN-γ treatment followed by 17 hours LPS (IFN-γ and LPS). Following treatment, fresh media was added to cells for 24 hours, then nitrite measurements at 543 nm were performed. *p<0.001.
Figure 3B:
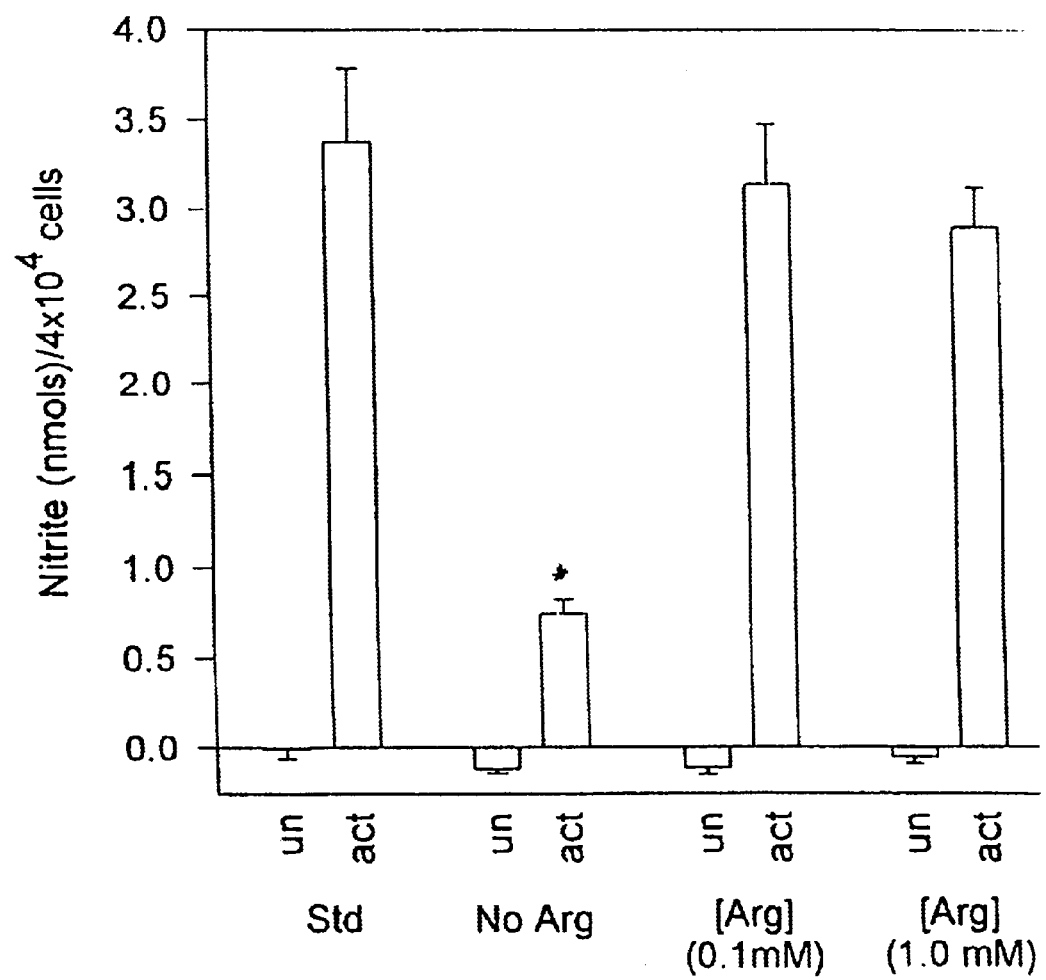
FIG. 3B illustrates the extracellular L-arginine requirement for nitric oxide production in activated J774 cells. macrophages were either untreated (Unact), or activated (act) with IFN-γ (20 units/ml, 2 hours) followed by LPS (100 ng/ml, 17 hours). Fresh media was added for 24 hours, followed by nitrite measurements at 543 nm. Cells were cultured in: standard RPMI 1640 (std), RPMI 1640 minus L-arginine (No Arg), RPMI 1640 reconstituted with 0.1 mM ([Arg] 0.1 mM), or 1.0 mM L-arginine ([Arg] 1.0 mM). Data represents the mean±SEM of 4 independent experiments (*p<0.001). This difference is highly significant.

Nitrite levels rose significantly (p<0.001) in J774 cells (FIG. 3A) and in BMMs (data not shown) upon combined IFN-γ and LPS treatment, but not by IFN-γ and LPS alone (FIG. 3A). It was also observed that J774 macrophage-mediated nitric oxide synthesis was dependent on exogenous L-arginine (FIG. 3B) as a 78% reduction in nitrite production in the absence of L-arginine from the media (p<0.001; FIG. 3B).

The residual nitrite levels (std.; FIG. 3B) may reflect L-arginine in the serum. Nitrite levels were undetectable in the absence of serum, with cellular viability becoming compromised after prolonged exposure (data not shown). Nitrite levels were fully recovered with the addition of either 0.1 mM or 1.0 mM extracellular L-arginine (the latter being the concentration in RPMI 1640 media; FIG. 3B).

EXAMPLE 4
RNA Isolation and Northern Blot Analysis

Total RNA was isolated from macrophages inactivated or treated with IFN-γ (20 units/ml) for 2 hours and/or LPS (100 ng/ml) for six hours using 1.0 ml of RNA isolation solution (Advanced Biotechnologies, Ltd.) per 10 cm petri dish. PolyA+ RNA was isolated using oligo(dT)-Sepharose (New England Biolabs) columns.

Northern blot analysis was performed with Mφ-derived total RNA (30 μg was loaded per lane) using CAT1, CAT2 and iNOS (gift from Dr. Hume)-specific [32P]-dCTP random primed labeled DNA probes synthesized from full-length cDNA templates. Loading was standardized using an 18S rRNA oligo DNA probe. Blots were washed at high stringency in 0.1×SSC/0.1% SDS, 42° C. The autoradiographs were quantified by scanning densitometry (BioRad).

Figure 4:
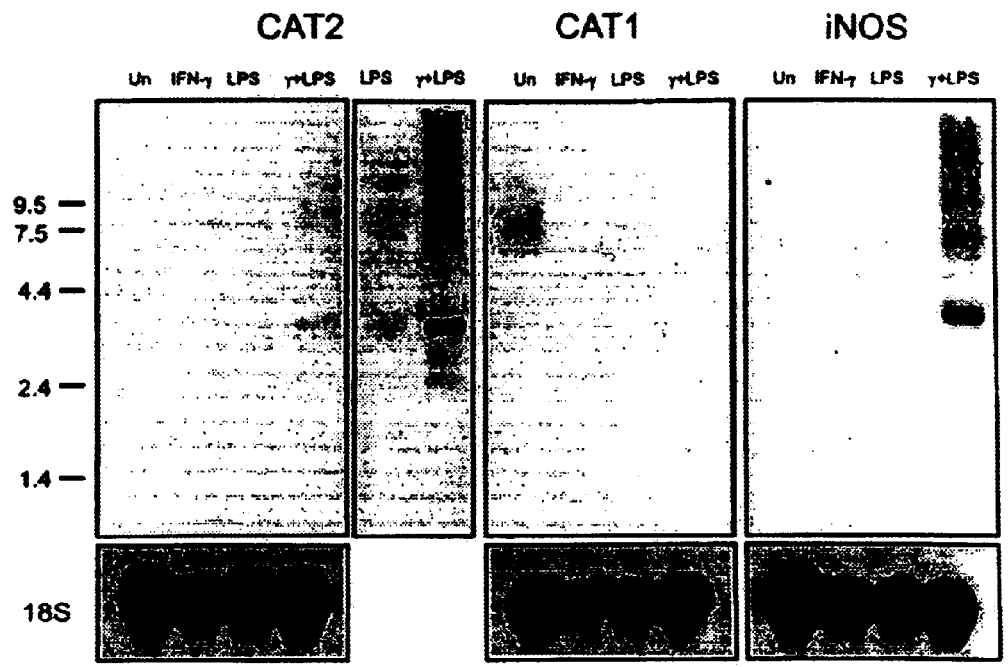
FIG. 4 shows CAT and iNOS mRNA expression in J774 cells by means of a Northern blot of total RNA (30 μg/lane) isolated from J774 cells cultured. Cells were either untreated (Un), treated with IFN-γ (20 units/ml) for 8 hours (IFN-γ) or with LPS (100 ng/ml) for 8 hours (LPS) or in combination of 2 hours IFN-γ treatment followed by 6 hours LPS (IFN-γ and LPS). Triplicate blots were hybridized with random primed probes synthesized from full-length CAT2 (3.9 kb), CAT1 (2.3 kb), or iNOS (4.1 kb) cDNA templates, loading control was a 18S rRNA oligonucleotide probe. For signal clarity, the CAT2 probed blot shows an additional longer exposure for LPS alone and IFN-γ and LPS.

The level of CAT2 mRNA (3.9 kb) was barely detectable in inactivated and IFN-γ-treated macrophages. It was faintly visible in LPS-treated cells and clearly visible (greater than 5-fold induction) in cells treated with both IFN-γ and LPS (FIG. 4, see Table 1 for mRNA quantitation). CAT1 mRNA (7.4 kb) levels decreased following treatment with IFN-γ, LPS, or combined IFN-γ and LPS (FIG. 4, see Table 1). iNOS mRNA (4.1 kb) paralleled CAT2 mRNA levels, being induced from undetectable levels (in the inactivated macrophages) to nearly 25-fold increases in the IFN-γ and LPS-treated cells (standardized to IFN-γ, see Table 1). IFN-γ or LPS alone do not significantly alter iNOS mRNA levels, this being consistent with nitric oxide production in J774 cells (FIG. 3A). Other L-arginine transporters, including 4F2hc and rBAT, were not detected by Northern blot analysis. However, 4F2hc (but not rBAT or CAT2a) was detected by RT-PCR in resting and activated J774 cells.

The increases in CAT2 mRNA (FIG. 4, Table 1) observed in activated macrophages also occurs in astrocytes treated with IFN-γ and LPS. In both of these cell types, there is an induction of iNOS and increased synthesis of nitric oxide. This suggests a common mechanism may exist for CAT2 mediated L-arginine transport induction, following IFN-γ and LPS activation in distinct nitric oxide-producing cell types.

TABLE 1

Induction of CAT and iNOS mRNA

| Condition | CAT2 | Cat1 Fold Change | iNOS |
|---|---|---|---|
| Unactivated | 1.0 | 1.0 | Undetectable |
| IFN-γ | 1.18 | 0.26 | 1.0 |
| LPS | 2.23 | 0.25 | 1.20 |
| IFN-γ + LPS | 5.88 | 0.11 | 24.7 |

EXAMPLE 5
Western Blotting

J774 total cell lysates were prepared by adding 1.0 ml RIPA buffer (1% deoxycholate, 1% Triton X-100, 0.1% SDS, 150 mM NaCl, 2 mM MgCl$_2$, 10 mM Tris-HCl, pH 7.2, 2 μg/ml aprotinin, 1 μg/ml pepstatin A, 0.5 μg/ml leupeptin) per 10 cm dish. The lysate was centrifuged 3 minutes at 12,000×g and the pellet discarded. Protein content was determined by either Lowry assay (BioRad, DC protein assay) or UV spectrophotometry readings at A280, which were shown to be similar.

Total cell lysates (60 μg/ml/ lane) were denatured with 6 M urea and separated by 10% SDS-PAGE. The proteins were electrophoretically transferred to supported nitrocellulose (Trans-blot, BioRad). The membranes were treated for 2 hours at room temperature with blocking buffer (5% milk/PBS/0.1% Tween-20/0.5M NaCl). They were then treated with anti-CAT2 antisera (1.0 μg/ml) for one hour with or without treating with GST or CAT2-carboxy terminus-GST fusion (pGEX-3X, Pharmacia) proteins (2.5 μg/ml in 4 ml), followed by secondary goat-anti-rabbit IgG (1:5,000, Bio-Rad) for one hour. All antisera incubations were in blocking buffer.

Proteins were detected by chemiluminescence (Renaissance, NEN Life Science Products) and the autoradiographs were quantified by scanning densitometry (Bio-Rad). Anti-Cat2 antisera were generated by injecting rabbits with CAT2-GST fusion proteins encoding the carboxy-terminal 70 amino acids, and the antisera was IgG enriched by protein A column and ammonium sulfate precipitation.

Figure 5:
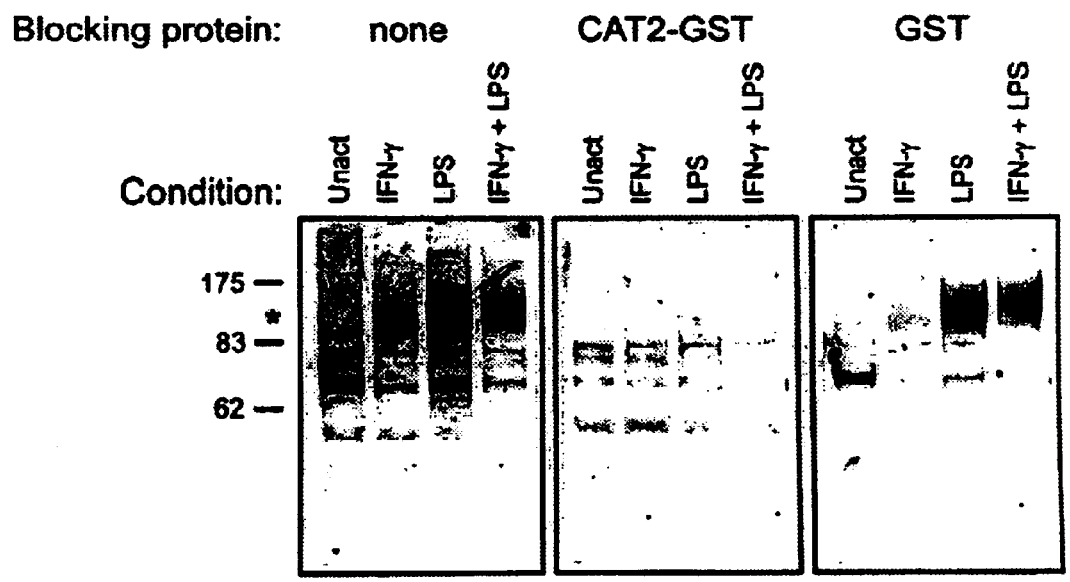
FIG. 5 illustrates CAT2 protein expression in J774 cells. Protein lysates were isolated from J774 cells which were either untreated (Unact), treated with IFN-γ (20 units/ml) for 2 hours (IFN-γ), or with LPS (100 ng/ml) for 17 hours (LPS), or in combination of 2 hour IFN-γ treatment followed by 17 hour LPS treatment (IFN-γ and LPS) and were separated (60 μg/lane) through 10% SDS-PAGE. Western blots were probed with anti-CAT2 antisera (1 μg/ml). Antibody specificity was tested using CAT2-glutathione S-transferase (GST) fusion protein (2.5 μg/ml), GST alone (2.5 μg/ml), or no blocking protein (none). * denotes CAT2 protein signal.

A large increase in CAT2 protein levels was observed in LPS alone or IFN-γ and LPS-treated cells (FIG. 5). CAT2 antisera specificity was shown by the detectable protein signal of 90 kilodaltons (kDa) competing with the immunogen CAT2-GST, but not GST alone (FIG. 5). The banding pattern was diffuse, reflecting extensive CAT2 glycosylation. Molecular weight of the CAT2 protein was larger than the sequence predicted size of 72 kDa, being consistent with previous reports.

EXAMPLE 6
Xenopus Oocyte Injection and Uptake

*Xenopus laevis* oocytes were isolated and prepared as previously described (Bertran, J. et al., *Proc. Natl. Acad. Sci.*, 89: 5601–5605 (1992); Markovich D. et al., *J. Biol. Chem.*, 268: 1362–1367 (1993)). Briefly, oocytes were surgically removed from *Xenopus laevis* frogs and de-folliculated using 2 mg/ml collagenase (Worthington Biochemical Corp.) in $Ca^{2+}$-free buffer (ORII: 82.5 mM NaCl, 2 mM KCl, 1 mM $MgCl_2$, 10 mM HEPES/Tris, pH 7.5) for 90 minutes, at room temperature. Oocytes were then washed with ORII followed by rinsing in modified Barth's solution (MBS: 88 mM NaCl, 1 mM KCl, 0.82 mM $MgSO_4$, 0.4 mM $CaCl_2$, 0.33 mM $Ca(NO_3)_2$, 2.4 mM $NaHCO_3$, 10 mM HEPES/Tris, pH 7.5, gentamycin sulfate 20 mg/l). The oocytes were incubated overnight at 17° C. in modified Barth's solution, and healthy stage VI oocytes were injected with 10 ng of polyA+ RNA isolated from inactivated and activated macrophages or water.

For 'hybrid depletion' or antisense inhibition experiments, mRNA (600 ng/μl) was denatured at 65° C. with specific oligonucleotides (100 ng/μl) in 50 mM NaCl. It was then allowed to slowly cool to room temperature. CAT2 oligos were: sense (5'-TATCCAAGACTTC-TTTGCCGTGTGC, 489–513 bp SEQ ID No. 1); antisense (5'-GTAGGCTGAAACCCTGTCCTTGC, 1406–1429 bp SEQ ID No. 2).

Fifty nanoliters of this solution was injected per oocyte, using a Nanoject (Drummond) oocyte injector and the oocytes were incubated at 17° C. for three days in MBS prior to uptake. Oocyte uptakes were then performed. Briefly, oocytes (at least ten per point), were washed 30 seconds in solution A (100 mM choline chloride, 2 mM KCl, 1 mM $CaCl_2$, 1 mM $MgCl_2$, 10 mM HEPES/Tris, pH 7.5). They were then placed in 100 μl of solution A containing 0.1 mM L-arginine and 20 μCi/ml [$^3$H]L-arginine for 30 minutes at room temperature. The uptake solution was subsequently removed and the oocytes were washed three times with ice-cold solution A. Individual oocytes were dissolved by SDS and radioactivity incorporated was counted by liquid scintillation.

Figure 6B:
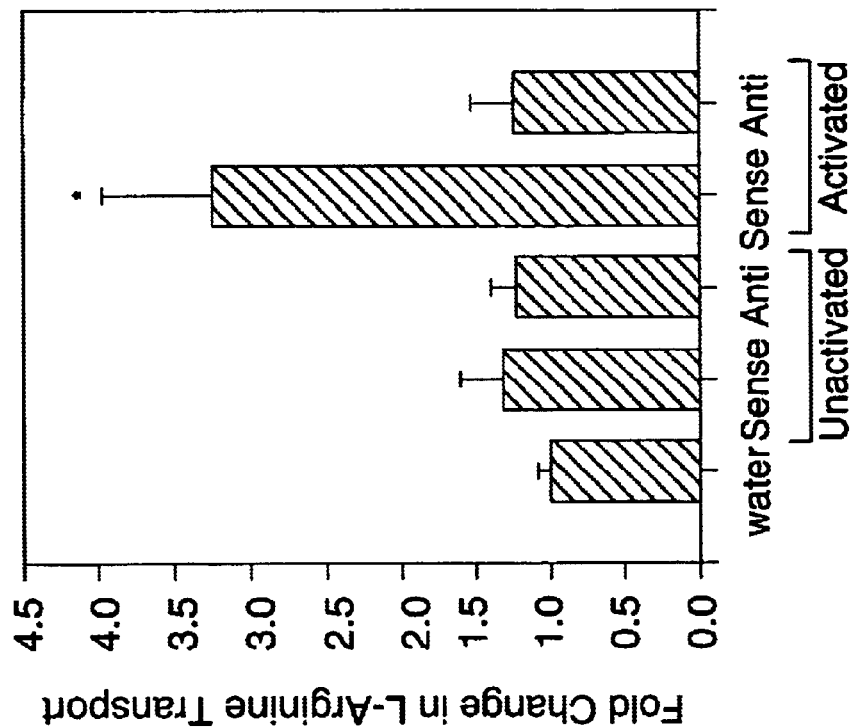
FIG. 6B demonstrates antisense inhibition of J774 mRNA-induced L-arginine transport in Xenopus oocytes. Oocytes were injected with either H$_2$O (water), mRNA (600 ng/μl) from untreated J774 cells (Unactivated) or mRNA (600 ng/μl) from J774 cells treated with IFN-γ (20 units/ml, 2 hours) and LPS (100 ng/ml, 6 hours; Activated). Prior to injection, mRNA was subjected to CAT2 sense (Sense) or antisense (Anti) oligodeoxyribonucleotide (ODN) hybrid depletion. The data is shown as -fold change in mRNA-induced L-arginine transport (in Xenopus oocytes) compared to controls (H$_2$O injected oocytes, water) and presented as the mean±SEM of three independent experiments (*p<0.001).
Figure 6A:
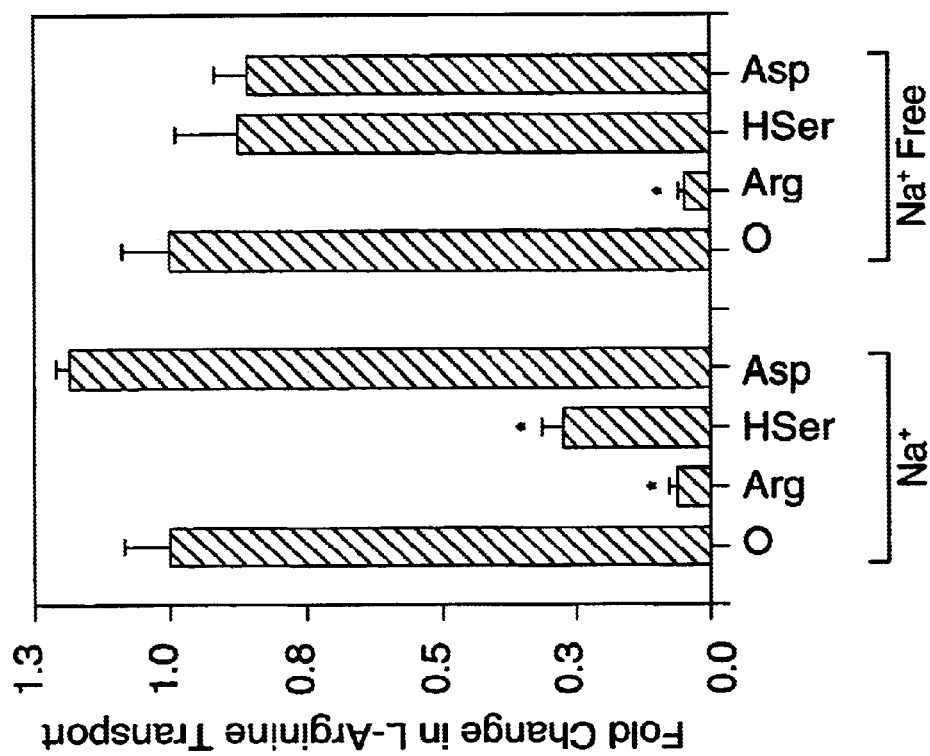
FIG. 6A depicts J774 Mϕ mRNA-induced L-arginine transport in Xenopus oocytes. Oocytes were injected with mRNA (600 ng/oocyte) derived from J774 cells activated with IFN-γ (20 units/ml, 2 hours) and LPS (100 ng/ml, 6 hours). [$^3$H]L-arginine uptake was performed in oocytes 3 days post injection, in the presence of (Na$^+$) or absence (Na$^+$-free; choline chloride substituted NaCl) of sodium, with either no inhibitor (0), or in the presence of L-arginine (Arg), L-homoserine (Hser), L-leucine(Leu) or L-aspartic acid (Asp), each at 5.0 mM concentration. Data is shown as -fold change in L-arginine transport, compared to control (no inhibitor, 0) and presented as the represents mean±SEM of four independent experiments (*p<0.001).

L-arginine transport in Xenopus oocytes was shown to be maximally induced by mRNA isolated from J774 cells primed with IFN-γ for two hours followed by 6 hour LPS treatment (data not shown). System y+ transport activity was induced in oocytes injected with mRNA from activated macrophages (FIG. 6A): L-homoserine significantly inhibited L-arginine transport only in the presence of Na+ (p<0.001). L-aspartic acid showed no inhibition (FIG. 6A).

The specific involvement of CAT2 in J774 L-arginine transport was addressed by hybrid depletion/antisense inhibition using CAT2 oligonucleotides. CAT2 specific oligonucleotides were annealed to J774 mRNA prior to injection and resultant mRNA induced L-arginine transport was measured in Xenopus oocytes.

Messenger RNA from activated J774 macrophages significantly induced L-arginine transport above controls (water injected oocytes; p<0.05; FIG. 6B). Injection of CAT2 antisense oligonucleotide reduced this transport back to control levels (CAT2 sense oligonucleotide had no effect). As a control, this same CAT2 antisense oligonucleotide also inhibited CAT2 cRNA induced L-arginine transport in Xenopus oocytes. mRNA from activated J774 cells injected into Xenopus oocytes led to a greater than 4-fold increase in nitric oxide production compared to mRNA from inactivated cells. It had a greater than 18-fold increase compared to endogenous activity (water injected oocytes; Table 2).

As with the induced L-arginine transport in Xenopus oocytes (FIG. 6B), CAT2 antisense oligonucleotides reduced elevated nitrite levels in Xenopus oocytes produced by mRNA from activated J774 cells suggesting CAT2 protein expression was important for nitric oxide synthesis.

EXAMPLE 7
Expression of CAT Transcripts in Tissues of Stressed and Unstressed Animals CAT1, 2 and 2a transcripts were examined in liver and skeletal and smooth muscle, organs involved in amino acid homeostasis, when animals and cells were subjected to specific stresses or activators. Abundant CAT2a liver expression is seen and this expression is not altered in response to food deprivation or partial hepatectomy (a procedure that induces mitosis in the majority of the remaining hepatocytes). Surprisingly, CAT2a transcripts accumulate in skeletal muscle in response to surgical trauma and fasting, while neither of the other forms, CAT1 or CAT2 are detectably altered in response.

Expression of CAT transcripts was also examined in T-cells and macrophages, cell types with special L-arginine requirements in response to immune challenge. Both CAT1 and CAT2 transcripts accumulate when T-cells are mitogenically activated, but with distinct kinetics. Activated macrophages accumulate CAT2 and iNOS messages with parallel kinetics suggesting that CAT2 mediated L-arginine transport may regulate the L-arginine:nitric oxide pathway. CAT2 promoter utilization was also assessed during each of the stress or activation responses (Example 12).

EXAMPLE 8
Surgical and Dietary Manipulation of Mice

Female AKR/J mice, 6 weeks of age were obtained from Jackson Laboratories, Bar Harbor, Me. Surgery was performed on mice anesthetized with 70 mg of sodium pentobarbital per kg body weight; either the entire spleen or 60–65% of the liver was removed and RNA prepared. Sham surgery was identical to the partial hepatectomy except the organs remained intact. After 0, 24 or 48 hrs. or 7 days mice were euthanized and RNA was prepared from liver, skeletal muscle (soleus and gastrocnemius), and uterus of partially hepatectomized, splenectomized or anesthetized control mice. Fasting studies were carried out with mice deprived of food for 24 or 48 hrs. after which they were euthanized and RNA prepared from specific organs.

EXAMPLE 9
Preparation of Splenocytes and Macrophages

Isolated splenocytes (MacLeod, C. L. et al *Mol. Cell. Biol.*, 10:3663–3674 (1990); Coligan, J. E. et al., eds., *Current Protocols in Immunology* Vol. 1, Chapter 3. Greene Publishing Associates and Wiley-Interscience, New York, 1992) from 6–8 week-old mice were seeded at 6×10$^6$ cells/ml in DMEM supplemented with 10% fetal calf serum, 2 mM glutamine with streptomycin and penicillin. The T-cell population was stimulated with 20 mg/ml of Concanavalin A (ConA) and RNA prepared at intervals. J774 mouse macrophages were cultured in RPMI 1640 medium in the presence or absence of LPS (100 ng/ml) and IFN-g (10 units/ml). Care was taken to avoid endotoxin contamination of reagents.

EXAMPLE 10
Preparation of Radiolabeled Probes
Probes for Northern blot analysis were a 2.4 kb EcoRI fragment of CAT1 cDNA, a 2.1 kb MscI fragment of CAT2 cDNA, full-length iNOS cDNA (from Dr. Hume), a 0.7 Pst1/BamH1 fragment from cyclophilin cDNA and a 0.2 kb Aval fragment from 18S ribosomal cDNA (ATCC). Isolated cDNA fragments were labeled with [$^{32}$P-]dCTP by random priming (Amersham) and labeled DNA purified on a NACS-52 column (Gibco BRL). Oligonucleotides (22mers) encoding CAT1, CAT2, and CAT2a, or iNOS were 5'-end labeled with [$\gamma$-$^{32}$P] ATP.

EXAMPLE 11
RNA Preparation and Analysis
Preparation of total RNA from cultured macrophages, splenocytes, or tissues and Northern blot analysis (10 μg/lane) used standard methods as described (Bertran, J. et al., *Proc. Natl. Acad. Sci.*, 89: 5601–5605 (1992)). The membranes were exposed to XOMAT film (Kodak) within the linear range of detection. The amount of RNA loaded and transferred was assessed by stripping blots and sequentially probing with either murine cyclophilin or 18S ribosomal cDNA. Autoradiographs of Northern blots were quantitated by laser densitometry.

EXAMPLE 12
CAT2/2a Reverse Transcription-polymerase Chain Reaction (RT-PCR)
CAT2 mRNAs are transcribed from at least 4 distinct, widely spaced promoters and the transcripts contain 4 distinct sequences within the 5' UTR. Reverse transcription of total RNA (5 μg) from the mouse cell lines SL12.4 (T-lymphoma) and J774 (Mφ); mouse liver and skeletal muscle tissues; and from unstimulated and stimulated splenocytes was used to detect CAT2 promoter usage. The CAT2 and CAT2a isoforms were distinguished as follows: the RT reaction was primed with 5'-CGCGAATTCCGACT-GTCGTGTGGGCAG-3' (1453–1470 nt, SEQ ID No. 3) located in a region 3' of the spliced exons. The PCR primers were nested within the transcribed region and flanked the alternately spliced region: 5'-TATCCAGACTTCTTTG-CCGTGTGC-3' (489–513 nt SEQ ID No. 4) and 5'-GTAGGCTGAAACCCTGTCCTTGC-3' (1406–1429 nt SEQ ID No. 5). The PCR products were authenticated using CAT2 and CAT2a specific 5'-end labeled oligonucleotides, CAT2: 5'-TCCCAATGCCTCGTGTAATCTA-3' (1071–1093 nt SEQ ID No. 6); CAT2a: 5'-TGCAGTCATC-GTGGCAGCAACG-3' (1159–11810 nt SEQ ID No. 7).

Figure 7:
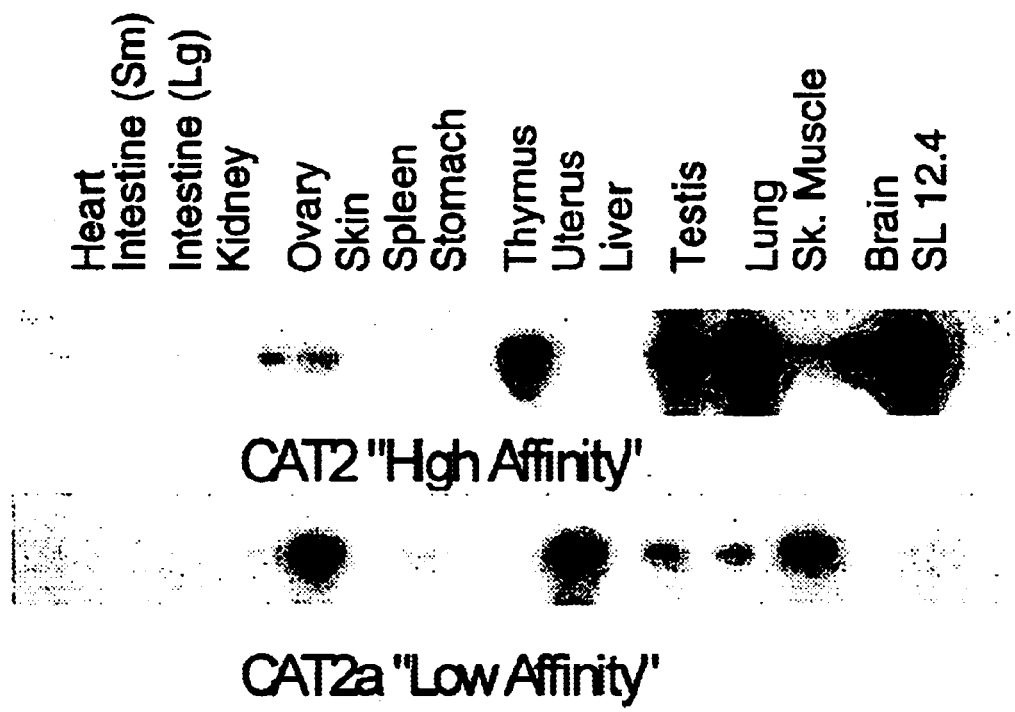
FIG. 7 shows CAT expression in normal mouse tissues. The Southern blot of the 15 indicated mouse tissues distinguished CAT2/2a isoforms. Total RNA from the indicated tissues were reverse transcribed, PCR amplified, Southern blotted and probed with CAT2 and CAT2a specific oligonucleotides.

EXAMPLE 13
CAT2 and CAT2a Tissue Distribution via RT-PCR Analysis
Prior to the identification of the CAT2a isoform, CAT2 transcript expression had been reported in a variety of cell lines, tissues and organs (e.g. Kakuda et al., *Transgene*, 1:91–101 (1993)). To determine which CAT2 isoform is expressed in normal organs under steady state conditions, RNA from these tissues was analyzed by RT-PCR (FIG. 7). The low affinity CAT2a isoform is expressed in skeletal muscle and liver, tissues with low amounts of the high affinity CAT1 or CAT2 isoforms. Reciprocal expression of the high and low affinity transporters is reasonable if they play different roles in the import or export of their substrates.

EXAMPLE 14
CAT Transcripts Increase in Lymphocytes Following Activation
Although CAT1 RNA is abundant in resting lymphocytes, these cells transport little L-arginine and L-lysine. However, following activation, L-arginine transport becomes necessary and is induced. CAT2 and CAT1 expression were compared following selective activation of splenic T-cells with Concanavalin A (Con A). CAT1 and CAT2 accumulate with distinct kinetics and to different extents. CAT1 mRNA is the predominant transcript and it accumulates 6-fold from 0–3 hours, when it gradually decreases to baseline by 24 hrs. Although the relative induction of CAT2 was underestimated at 16 fold (as it is undetectable in resting cells, it was normalized to the 3 hour sample), the CAT2 induction parallels the increase in y$^+$ transport activity. Discrimination of the CAT2/2a isoforms was achieved on Southern blots of RT/PCR products probed with highly specific oligonucleotides Small amounts of CAT2, but no CAT2a mRNA was present in unstimulated T-cells whereas no CAT2 was detected using the less sensitive Northern analysis. Based on the timing of CAT2 induction, it is likely to be responsible for the induced system y$^+$ transport activity observed in activated T-cells. CAT2 gene transcription was previously shown to initiate from several distinct promoters in cultured SL12.4 T-cells. This differential promoter usage generates multiple unique mRNAs containing promoter specific 5'-untranslated regions (5'-UTRs). These unique 5'UTRs were exploited to ascertain promoter usage in freshly isolated quiescent and activated T-cells by RT/PCR. Splenocytes only use the most distal CAT2 promoter 1A prior to and following activation. In contrast, the SL12.4 T-lymphoma cell line uses at least 4 distinct promoters.

Figure 8A:
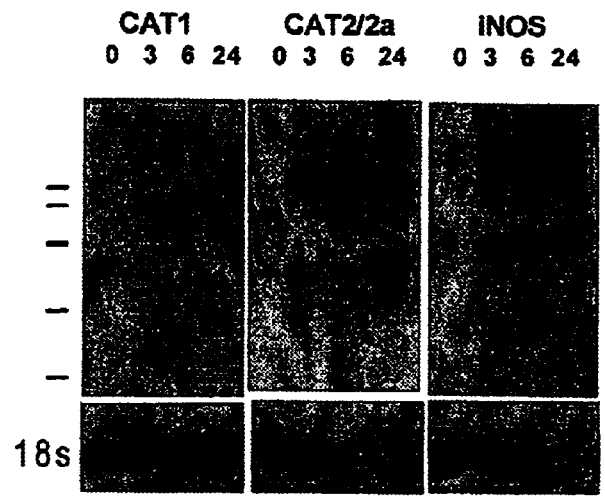
FIG. 8A shows coordinate induction of CAT2 and iNOS in activated J774 macrophages via Northern analysis of CAT and iNOS expression from inactivated J774 macrophages (0 hours) or following addition and incubation of LPS and IFN-γ for 3, 6, and 24 hrs as indicated. Blots were probed with CAT1, CAT2/2a, iNOS and 18S cDNA probes.
Figure 8B:
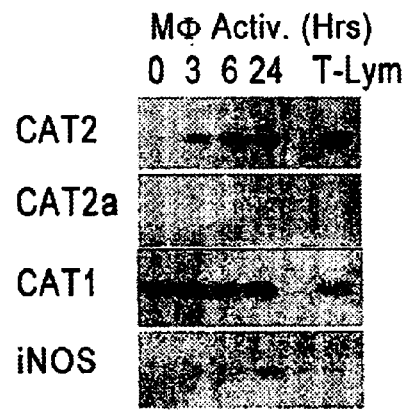
FIG. 8B demonstrates RT/PCR analysis of CAT and iNOS expression in activated J774 macrophages.
Figure 8C:
FIG. 8C shows a Western blot of cell lysates from J774 macrophage cells unactivated or activated for 24 hrs and probed with anti-CAT2 antisera. Arrowhead indicates the CAT2 specific reactivity that migrated

EXAMPLE 15
CAT mRNA Expression in Inactivated and Activated Macrophages
Macrophage activation by cytokines and LPS results in the induction of iNOS mRNA and protein together with a coordinate increase in L-arginine transport via system y$^+$. Activated macrophages produce large amounts of nitric oxide for a sustained period, this iNOS-mediated nitric oxide synthesis requires extracellular L-arginine. To determine which transporters contribute to transport system y$^+$ mediated L-arginine uptake, J774 macrophages were activated with LPS and IFN-γ.
Northern analysis (FIG. 8A) shows that CAT1 is expressed in inactivated cells and does not increase during activation, but, instead, they actually decrease by 24 hours following activation. In contrast, CAT2 and iNOS mRNAs increase in parallel from undetectable levels in unstimulated cells to substantial amounts by 3 and 6 hours. Only the high affinity CAT2, but not the low affinity CAT2a transcript was detected using RT/PCR (FIG. 8B). CAT2 protein is also induced from undetectable levels in unactivated cells to abundant expression in LPS/IFN-activated cells (FIG. 8C). From this data, it appears that CAT2 is responsible for the increase in system y$^+$ transport induced in activated macrophages. CAT2-mediated L-arginine transport may be required to supply iNOS with one of its essential substrates. Like splenocytes, promoter A is used exclusively by activated and inactivated J774 macrophages, RAW 264.7 macrophage cells and inflammatory peritoneal macrophages. Hence, the use of promoter A during CAT2 induction is common to J774 cells, RAW 264.7 cells and macrophages immediately isolated from animals.

EXAMPLE 16
CAT mRNA Expression in the Liver

Figure 9A:
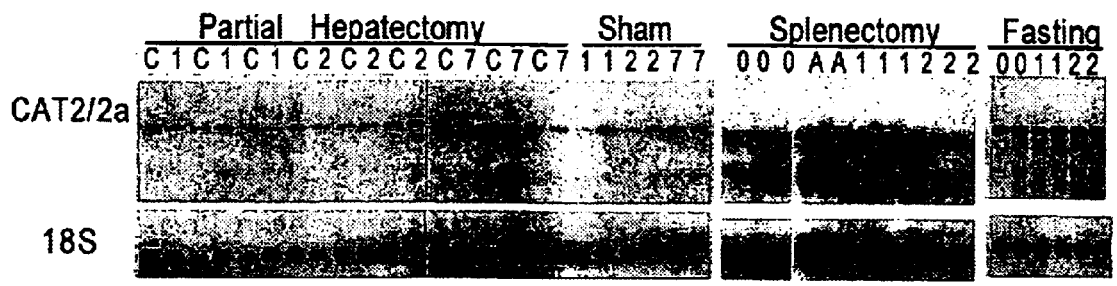
FIG. 9A shows (Left) CAT2 mRNA in liver following partial hepatectomy, splenectomy and fasting using Northern analysis of CAT2 expression from a representative group of RNAs prepared from liver 1, 2 or 7 days following partial hepatectomy (H) or sham (S) surgery and from resected liver (0). The blots in panels A–C were subsequently probed with cyclophilin (Cyclo) to estimate the amount of CAT2 RNA in each lane. Middle: Northern analysis of liver CAT2 mRNA following splenectomy (SP) or anesthesia without surgery (A). Right: A similar analysis of CAT2 expression in liver following food deprivation.
Figure 9B:
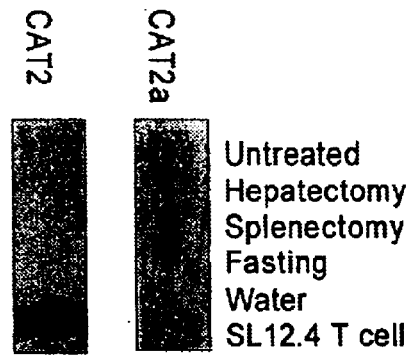
FIG. 9B is an RT/PCR analysis of CAT2 and CAT2a expression in liver following hepatectomy, splenectomy, and fasting (24 hours).
Figure 9C:
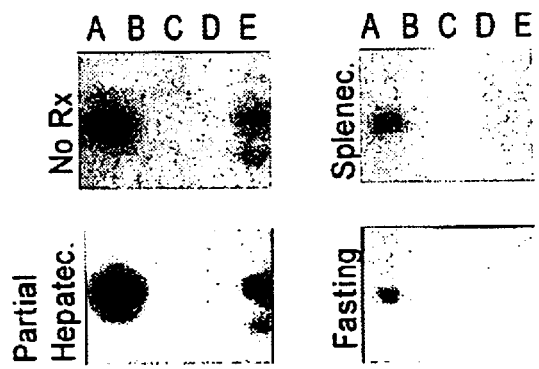
FIG. 9C illustrates CAT2 promoter usage in liver following the treatments. RNA was prepared separately from four to six animals in each treatment or control group; representative data is shown.

Normal adult liver expresses exclusively CAT2a transcripts, although both established hepatoma cell lines and freshly explanted hepatocytes accumulate CAT1 mRNA. It is not clear whether Cat1 gene expression in cultured normal and neoplastic hepatocytes is triggered by active cell proliferation or is a response of hepatocytes growing in monolayer culture. To address this question, the expression of both genes was examined during hepatocyte replication in vivo following surgical ablation of 60–70% of the liver. The remaining hepatocytes undergo DNA synthesis and mitosis 24 to 48 hours after surgery. FIG. 9A shows a Northern analysis of RNA from the resected (zero time) or regenerating liver from partially hepatectomized (H), sham-operated (S) or anesthesia control (A) animals. The data show no significant change in CAT2 transcripts 24 or 48 hours following surgery. Likewise, surgical trauma per se failed to significantly alter CAT transcript quantities in the liver (data not shown). Although CAT1 mRNA was not detectable in regenerating liver 24 or 48 hours later, low, transient expression of CAT1 mRNA in liver 4–6 hours following hepatectomy has been reported (Wu et al., *J. Virol.,* 68:1615–1623(1994)). This expression was no longer detectable 24 hours post hepatectomy, when cells were undergoing mitosis. Furthermore, only CAT2a and not CAT2 is expressed in liver following partial hepatectomy, splenectomy or fasting (FIG. 9B). CAT2 promoter usage remained unchanged following surgery and fasting (FIG. 9C). Anesthesia itself had no significant effect on CAT2a mRNA expression 24 hours later (FIG. 9A).

As plasma levels of arginine are modulated by diet, the effect of fasting, which increases ammonia production and arginine utilization by stimulating gluconeogenesis was assessed. Fasting failed to elicit a change in either CAT1, CAT2 or CAT2a mRNA levels in liver (FIG. 9A). It is concluded that CAT2a mRNA is constitutively expressed at nearly constant levels in the liver, whether hepatocytes are quiescent or replicating and regardless of dietary L-arginine availability. Hence, CAT1 expression in isolated hepatocytes is likely to be a response to cell culturing conditions and not cellular proliferation.

EXAMPLE 17
CAT mRNA Expression in Skeletal and Smooth Muscle

Figure 10A:
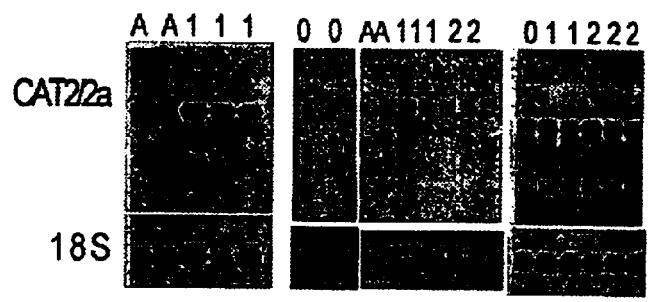
FIG. 10A Left: Northern analysis (10 μg.lane) of skeletal muscle CAT2/2a mRNA expression one day following partial hepatectomy (lanes labeled 1) or the anesthesis control(A) or from untreated mice(0). Middle: Northern analysis of skeletal muscle CAT2/2a mRNA expression following splenectomy. Right: Northern analysis of skeletal muscle following 1 or 2 days of fasting all compared to 18S ribosomal RNA as a control for loading.

Surgical trauma results in the loss of substantial protein mass from skeletal muscle and fasting induces skeletal muscle catabolism to provide circulating amino acids. Since both CAT1 and CAT2 are co-expressed in skeletal muscle, it was of interest to test whether surgical trauma or fasting altered their expression. FIG. 10A shows a representative Northern analysis of skeletal muscle expression that illustrates that CAT2/2a transcripts are substantially induced whereas CAT1 mRNA levels remain low and unaltered. The most pronounced increase, 8.7 fold (p=0.03), occurred one day after hepatectomy (FIG. 10A). This increase was linked to liver regeneration, since it was not observed in sham-operated animals. Two days after hepatectomy, CAT2a mRNA had returned to control levels. Splenectomy also significantly induced CAT2a mRNA 3.5 fold (p=0.001) and it decreased to 2.1 fold above baseline two days later (p=0.03). Finally, fasting one day produced a 2.4 fold significant increase (p=0.0005). CAT1 mRNA levels were not significantly altered by these treatments.

Figure 10B:
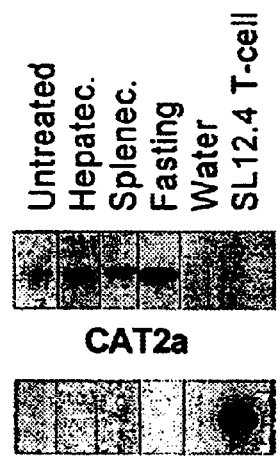
FIG. 10B shows the RT/PCR analysis of CAT2 and CAT2a isoform expression in skeletal muscle following the indicated conditions.
Figure 10C:
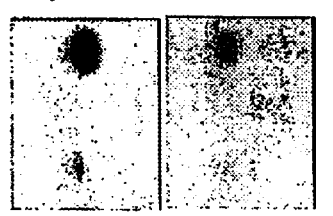
FIG. 10C shows the promoter usage in skeletal muscle following the indicated treatments. The letters designate the distinct CAT2 promoters.
Figure 10C:
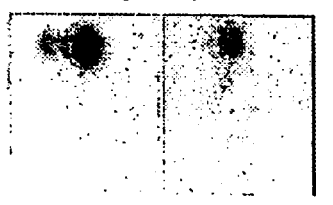

Interestingly, only the isoform CAT2a was induced in response to hepatectomy, splenectomy and fasting (FIG. 10B). Perhaps the expression of the low affinity CAT2a isoform spares the muscle cell from lethal release of its L-arginine stores. Only a subtle change in promoter usage was detected in skeletal muscle following hepatectomy (FIG. 10C). Similar to macrophages and lymphocytes, the promoter 5' of exon 1A is used in skeletal muscle following hepatectomy, splenectomy, and fasting. As yet, this utilization of the 1D promoter is the only condition in whcih promoters other than 1A are utilized except in cell lines. This promoter usage clearly does not dictate the selection of splicing events that produce CAT2/2a isoforms, since it is used exclusively in lymphocytes and macrophages which express the high affinity CAT2 isoform and in liver, where only the low affinity isoform is expressed. Promoter D is only used in skeletal muscle following partial hepatectomy (FIG. 10C), and thus this promoter may be active during liver regeneration. This data shows that the CAT2 promoter 1A is predominant in all tissues and cell lines examined regardless of the stresses applied, the tissue examined, or which alternate splicing event occurs during processing of the transcript.

Cat gene expression was additionally assessed in uterine smooth muscle, which preferentially expresses CAT1 mRNA. Neither hepatectomy, splenectomy nor fasting altered the expression of Cat1 or CAT2 in uterine muscle (data not shown) in response to the same conditions that stimulated CAT2a mRNA expression in striated muscle. Unlike skeletal muscle, the uterus expresses only the CAT2 and not the CAT2a isoform. Hence, CAT2a induction is specific for skeletal muscle, and is not induced in this smooth muscle.

EXAMPLE 18
A Model System to Examine CAT2 and iNos in Mammary Tumors: the mTag Oncogenic Transgene Model for Breast Cancer in Mice The mTag oncogenic transgene elicits multifocal metastatic mammary adenocarcinoma in 100% of the female mice carrying it. The mTag oncogenic transgene serves, when expressed in the iNos$^{-/-}$ and Cat2$^{-/-}$ mice, to define the roles of iNos and Cat2 in breast tumor progression.

Although the mouse has been used as a model for a number of individual steps in the metastatic cascade, a spontaneous mouse model for the entire process has not been developed. Often, poor penetrance of the metastatic phenotype of spontaneous mouse tumors presents difficulties. A number of transgenic animals, however, have been found to metastasize extensively, possibly due to the accelerated nature of the disease (Guy, et al., *Mol. Cell Biol.,* 12:954–961 (1992); Guy et al., *Genes and Dev.,* 8:23–32 (1994)). These animals develop metastatic disease in a heritable and highly penetrant manner. One particularly interesting and useful transgenic model is the MMTV-polyoma middle T (mTag) transgenic mouse. mTag elicits mammary tumors and extensive pulmonary metastases (Guy, et al., *Mol. Cell Biol.,* 12:954–961 (1992)).

Female mTag transgenic mice develop synchronously appearing multifocal tumors in 5–6 of their 10 mammary glands within 60–90 days following birth (dpp), independent of pregnancy. Males also develop mammary and salivary tumors, although with a much longer latency. Importantly, more than 95% of the animals develop pulmonary metastases by 100 days. The high penetrance and extensive metastatic properties of the tumors make it an excellent model to combine with knockout genes to elucidate the participation of test genes in mammary tumor development and progression.

EXAMPLE 19
Development of the mTag/iNos Mouse Strains

The mammary gland and mammary tumorigenesis presents two major experimental advantages: 1) CAT2 is expressed in mouse and human mammary glands; and 2) iNOS expression has been documented in mammary tumors, mammary tumor cell lines, and in macrophages that infiltrate the mammary gland. Hence, animal models of mammary tumorigenesis that would be suitable for the analysis of iNOS and CAT2 arginine transport were evaluated. A particularly valuable one, described above, was developed by Dr. William Muller of McMaster University (Guy, et al., Mol. Cell Biol., 12:954–961 (1992)). This transgene has been dubbed mTag or mPyV and it has been used to assess particular steps and signaling pathways in mammary tumorigenesis (Guy, et al., Mol. Cell Biol., 12:954–961 (1992)).

Mammary tumorigenesis in general, and this strain in particular, have several very important and useful features: (1) female mice develop multifocal mammary tumors by 90 days of age; (2) these tumors metastasize to the lung in 95% of animals by 100 days of age; (3) the tumors induced by the expression of mTag are adenocarcinomas that closely resemble human breast adenocarcinoma; (4) the mammary gland is outside the body cavity, and tumors can be detected early and monitored easily; (5) epithelial hyperplasia is apparent at weaning and ultimately progresses to clonal, angiogenic, metastatic tumors in several mammary glands—hence this system offers a model to test gene effects on multistep carcinogenesis; (6) the mammary gland undergoes almost all development after birth, at puberty and pregnancy; and (7) transplantation studies are both feasible and informative.

Figure 11:
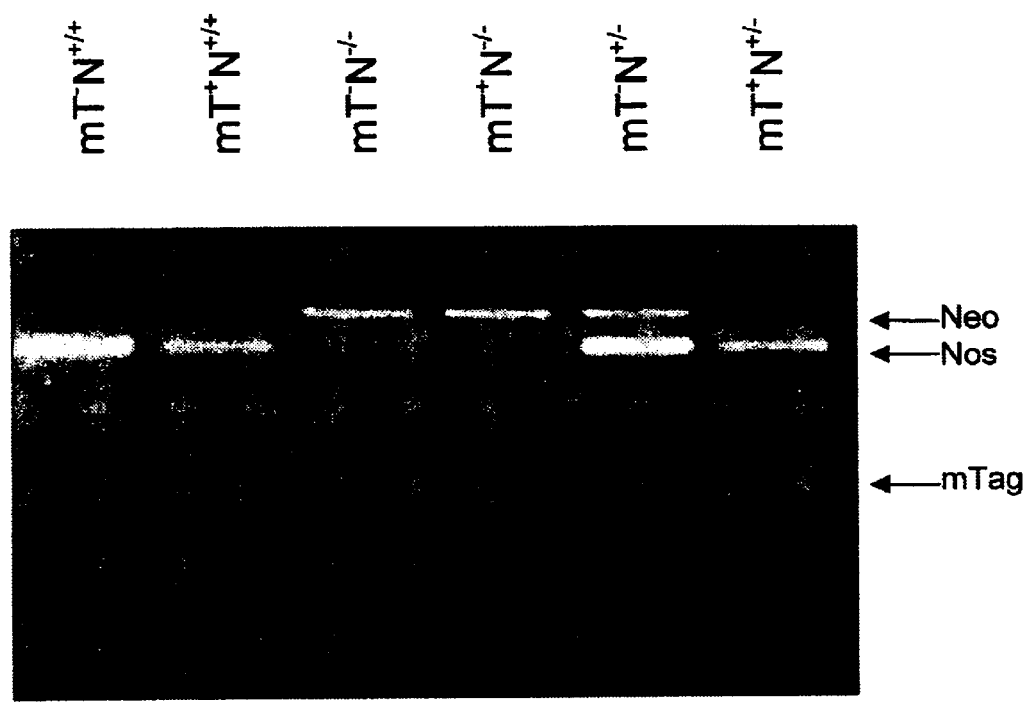
FIG. 11 depicts PCR analysis of the mTag, iNos genotype. Conditions have been established that permit the analysis of Nos, Neo and mTag DNA in a single reaction. DNA is prepared from a tail fragment isolated when mice are weaned and ear-tagged. The presence of PCR fragments for Neo determine that at least one iNos knockout allele is present, if there is also a Nos fragment, the genotype is $N^{+/-}$.

A mouse line lacking functional iNos, produced by Oliver Smithies (Laubach et al., Proc. Natl. Acad. Sci. USA, 92:10688–10692 (1995)) was available from the Jackson laboratory. iNos$^{-/-}$ breeding pairs and mTag mice were obtained and the required breeding conducted to obtain the following genotypes: 1) mTag$^{+/-}$ iNos$^{-/-}$ and 2) mTag$^{+/-}$ iNos$^{+/+}$ females. Genotype assays using PCR that easily diagnose the mTag and iNos genotype were developed (FIG. 11).

EXAMPLE 20
The Lack of Functional iNOS Delays Tumor Growth

Figure 12:
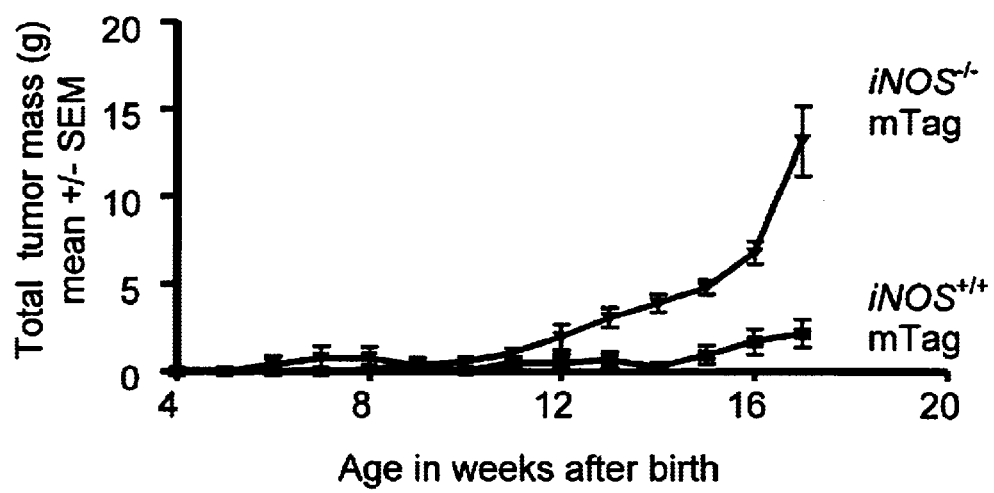
FIG. 12 shows the effect of iNos genotype on tumor burden. The oncogene mTag is present in both groups of mice. The squares (lower line) show the tumor mass in mice lacking nitric oxide production from iNOS. Mice were sacrificed at the times indicated when the mammary pads were dissected and weighed. The group represented by triangles (upper line) have normal production of nitric oxide from iNOS. Both groups received a normal diet. The difference in tumor growth is highly significant (p=0.0001).
Figure 13:
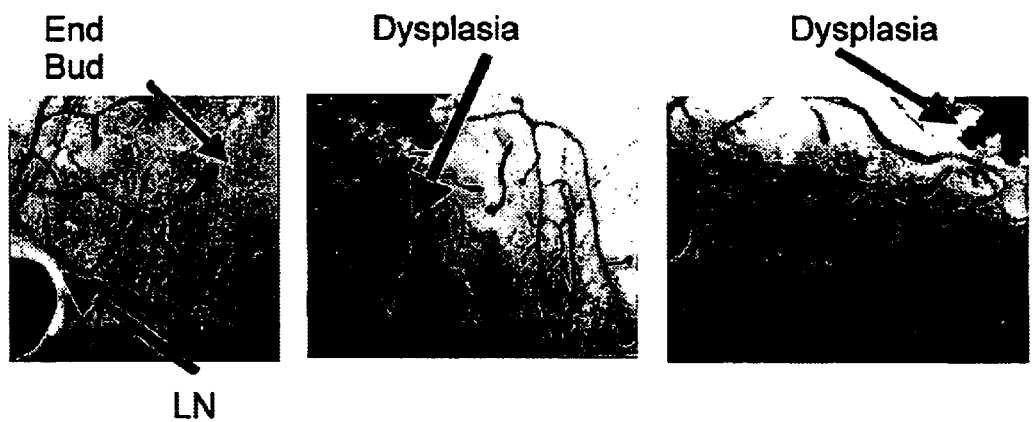
FIG. 13 shows mammary whole mount analysis of hyperplasia at 35 dpp. Glands were collected and prepared for whole mount analysis. There is no clear difference in the extent of hyperplasia between the Nos genotypes. Compared to wild type mice, there is extensive hyperplasia in samples from mTag mice. LN=lymph node.

A pilot study was conducted to determine whether iNos genotype modulates mTag-induced tumorigenesis. A time course of tumor growth was carried in mTag/iNos$^{+/+}$ or mTag/iNos$^{-/-}$. The mice in each group were followed up to 120 dpp. A total of 38 mice of each genotype (mTag$^{+/-}$/iNos$^{-/-}$ and mTag$^{+/-}$/iNos$^{+/+}$) were examined by palpation twice weekly (during weighing) until tumors were detected. Once detected, tumor sizes were measured weekly. The age of each animal was noted as the tumor became detectable. Five mice at 60, 75, 90, 105 and 12 mice at 120 dpp were sacrificed and each mammary gland was weighed. FIG. 12 shows the mean of total mammary weight (either weighed directly or estimated with calipers) with the standard error of the mean plotted. This data clearly shows that mice with intact iNos gene function develop mammary tumors significantly more rapidly than do the iNos knockout mice. This finding shows that any tumor protective effects of nitric oxide were overcome by stimulatory effects of nitric oxide on tumor progression.

For the mTag$^{+/-}$ transgenic females that contain at least one functional allele of iNos, the $T_{50}$ is 68 dpp. For mice lacking iNOS, the $T_{50}$ is 84 dpp. This value corresponds to the time (age) at which at least 50% develop at least one palpable mammary tumor. A map of tumors and their size was recorded from data accumulated to date, and there is no evidence that the degree of mammary epithelial dysplasia evident shortly after weaning differs significantly with iNOS genotype. Mammary whole mounts revealed a similar degree of mammary epithelial pathology in glands that lack a palpable tumor in both iNos genotypes.

EXAMPLE 21
Metastasis

Figure 14:
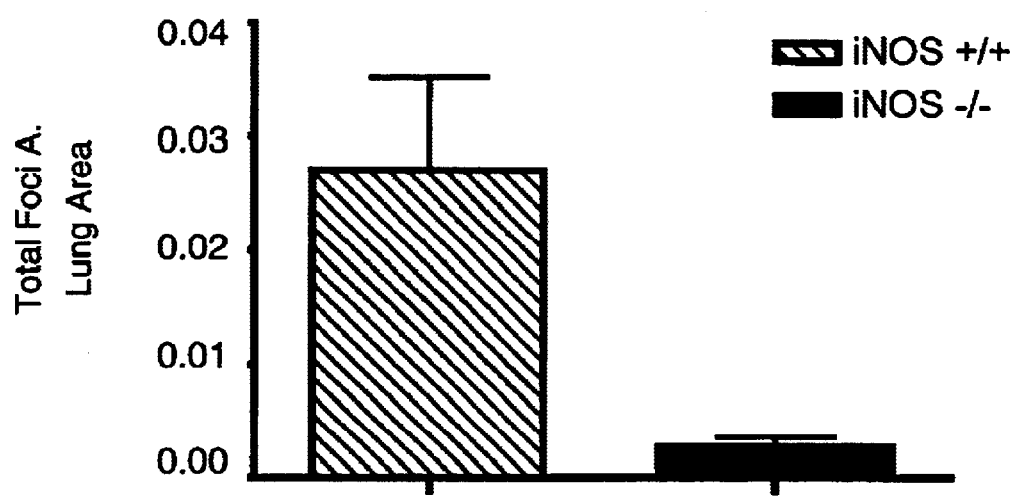
FIG. 14 is a comparison of the extent of metastasis between the iNos genotypes. The area comprising the foci was calculated and expressed as a ratio of the total area examined using ImagePro 2.0 software on images captured by a digital camera.

To assess the extent of lung metastasis at 105 and 120 dpp, lungs were collected. Fragments were used to prepare RNA and the remainder was divided for freezing in OCT embedding compound (Miles Lab) or fixed and embedded in paraffin. A detailed pilot analysis of the metastasis detectable in mice at 105 and 120 dpp was carried out. FIG. 14 shows this analysis of Nos–/– and Nos+/+ mice. This data was collected by measuring the ratio of the area occupied by metastatic foci to total area assessed in fixed and embedded sections stained with hematoxylin and eosin.

The fact that Nos$^{-/-}$ mice have fewer and smaller pulmonary metastases is not particularly surprising since the tumor burden of the Nos deficient mice is substantially lower than Nos wild type mice. However, it is clear that β-casein (a milk protein) becomes detectable in the lung long before any visible pulmonary foci are apparent. Furthermore, a perfect correlation between the presence of visible pulmonary foci at 105 days and the presence of a detectable RT/PCR β-casein product has been observed.

EXAMPLE 22
Vascular Density of the Established Tumors

Figure 15:
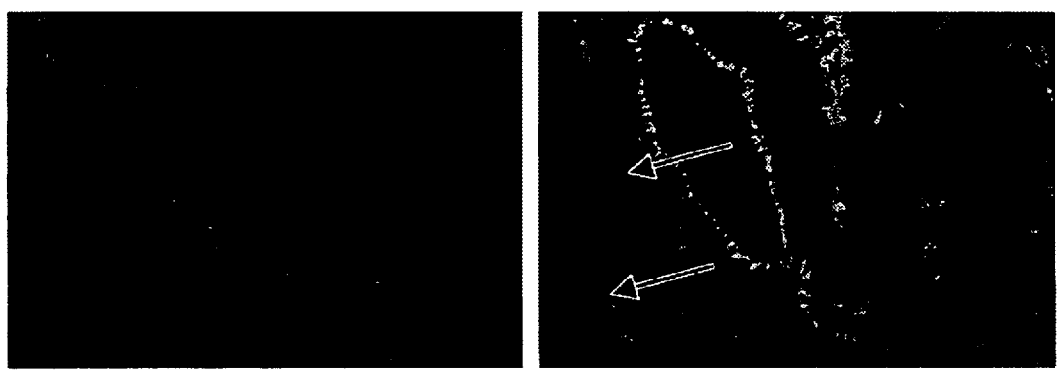
FIG. 15 shows an angiogenesis assay on a mammary tumor sample. Frozen sections from an $iNos^{+/+}$ mammary tumor were blocked and subsequently incubated simultaneously with anti-Factor VIII (rhodamine, left panel) and anti-CD31 (fluorescein, right panel) monoclonal antibodies. Arrows point to newly forming blood vessels that are not yet mature enough to express Factor VIII.
Figure 16:
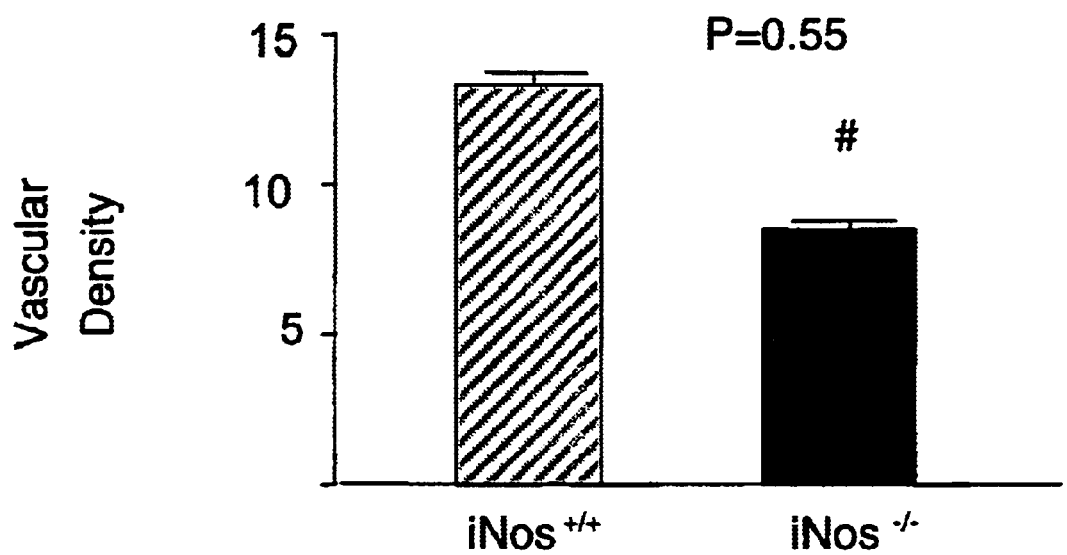
FIG. 16 demonstrates that vascular density in the $iNos^{-/-}$ tumors is lower than in the $iNos^{+/+}$ tumors.

To examine the vascular density of established tumors in both genotypes, CD31 (PCAM) antisera (PharmaGen) was used as a marker for new blood vessel formation. FIG. 15 shows a representative section through a mammary tumor from Nos wild type mice documenting the extensive neovascularization of the tumor. Standard methods were used to count the new blood vessels (e.g. Friedlander, M., et al., Science, 270:1500–1502 (1995)).

After staining and capturing the images on a digital camera, the CD31 positive signal in both iNos genotypes were quantitated. There is a trend that indicates that the iNos–/– have less extensive angiogenesis compared to tumors from wild type mice.

Sections of whole mounted mammary gland tumors can also be assessed for $\alpha_v\beta_3$ expression to further distinguish neovasculature from established mammary blood vessels. Digital imaging assessment of the relative number of new blood vessels per unit area can then be determined. Tumor mass and relative amount of angiogenesis combine to give an overall picture of the differences in angiogenesis between the different genotypes. Use of a time course (60, 80 and 100 dpp) of angiogenesis helps to ascertain the effects of iNOS or CAT2 loss on neovascularization and rate of tumor growth. Tumor cell death is monitored by TUNEL assays in tissue sections. Primary tumor lysates are examined via Western blotting for p53 and p21, key proteins in apoptosis.

In addition to the neovascularization studies discussed above, the effect of iNos and Cat2 genotype on angiogenesis can be assessed directly. VEGF and bFGF-impregnated Elvax slow-release polymer pellets are implanted into the cremaster muscle of male mice with the appropriate genotype or into the mammary fat pad of females that either possess or lack the mTag transgene. Extent of angiogenesis induced is measured simply by counting using a grid.

EXAMPLE 23
Establishment and Analysis of Mammary Tumor Cell Lines

Cell lines were established from the mammary glands of mTag/iNos$^{+/+}$ and mTag/iNos$^{-/-}$ mice by dissecting and mincing tumor tissue of 60 dpp females, followed by digestion with collagenase. The cells were plated with DMEM plus 10% fetal calf serum. Differential trypsinization over the next several weeks was used to enrich for epithelial cells. After about 2 months, the cultures became predominately epithelial and continued to grow rapidly. In fact, the epithelial nature of the cultures is evident at the outset, and these cells express low levels of β-casein, a milk protein marker, confirming their mammary epithelial origin. These cells can be stimulated to express iNOS protein following addition of several combinations of cytokines (FIG. 17).

Figures 17A, 17B, 17C:
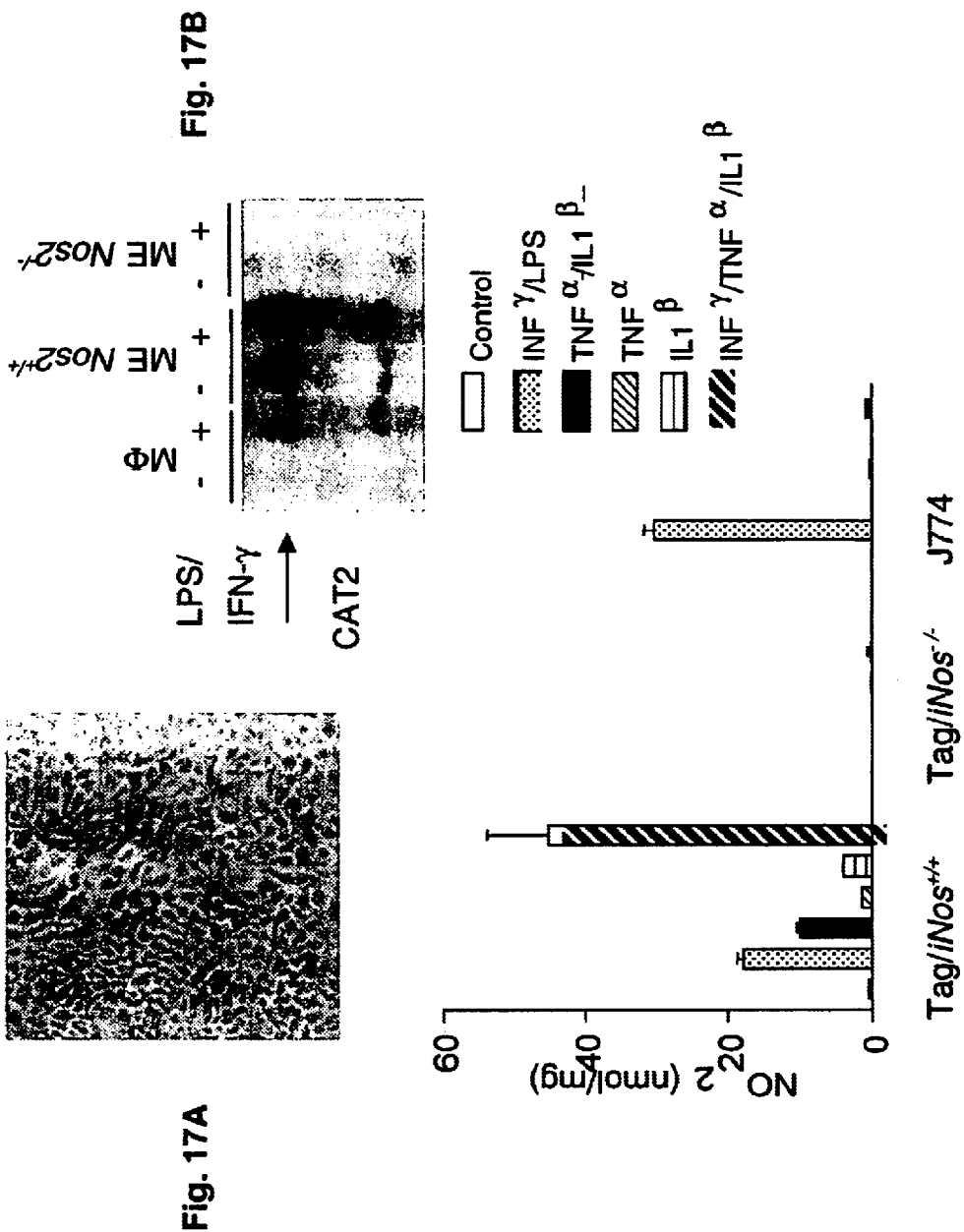
FIG. 17A shows that the epithelial nature of the cells is evident from their cobblestone morphology; both $iNos^{+/+}$ and $iNos^{-/-}$ cell lines display this morphology.
FIG. 17B is a Northern blot of LPS- and IFN-γ-treated cells from tumor cell lines from $iNos^{+/+}$ and $iNos^{-/-}$ mice and J774 macrophages. The RNA was probed with CAT2 and the blot shows that the $iNos^{-/-}$ cells fail to induce CAT2 whereas the macrophages and $iNos^{+/+}$ cells increase CAT2 mRNA following stimulation.
FIG. 17C demonstrates the same cell lines as in FIG. 17B, cultured in triplicate with or without the indicated cytokines for 17 hours, washed and then cultured without stimuli for 24 hours. Media was then collected and NO2 measured. As expected, nitric oxide is not detectably produced by $iNos^{-/-}$ cells regardless of stimuli; $iNos^{+/+}$ cells produce nitric oxide only following stimulation. J774 macrophages synthesize nitric oxide only in response to LPS/IFN-γ. Concentration of NO2 was determined from a standard curve normalized for mg protein.

The data shown in FIG. 17B reveal a surprising result. CAT2 mRNA and arginine transport increase substantially when cells are stimulated to produce iNOS and nitric oxide. It is noteworthy that the Nos$^{-/-}$ cells express no detectable CAT2 mRNA either before or following stimulation with any of the cytokine combinations tested. This data suggests that CAT2 mRNA accumulation may be regulated directly or indirectly by iNOS. The unstimulated cells also lack detectable Cat2 expression while the wild type cells express low levels of CAT2 mRNA.

EXAMPLE 24
CAT2 Knockout Mice

Figures 22A, 22B, 22C, 22D:
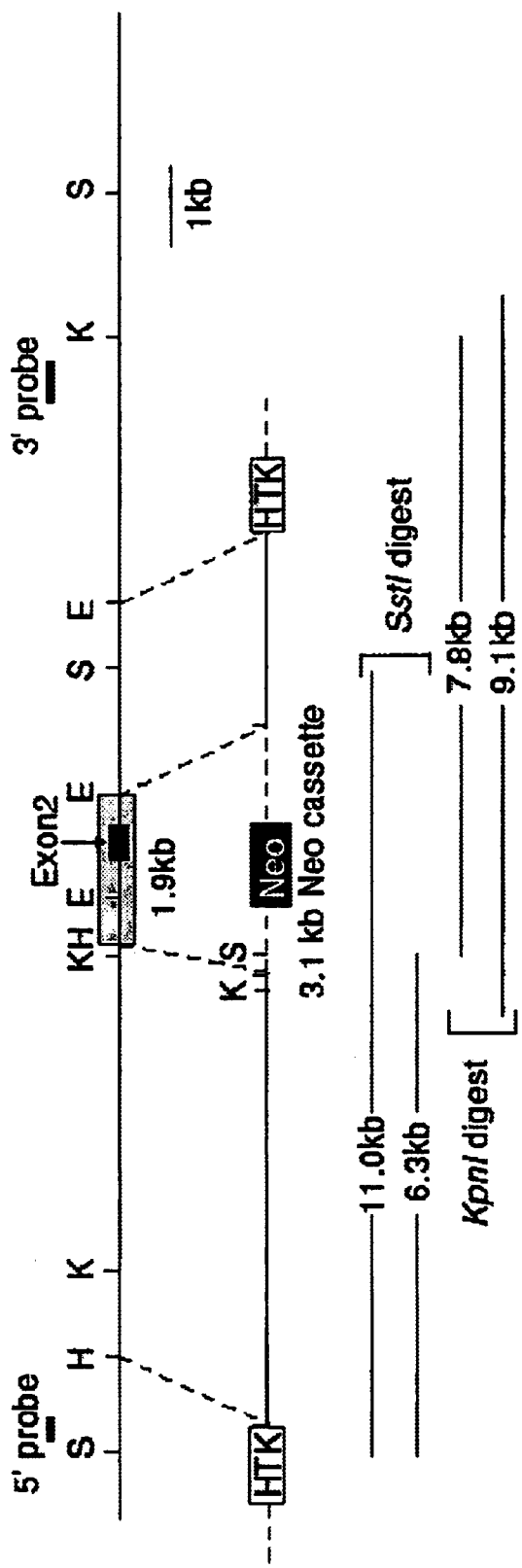
FIG. 22A shows the construction of the Cat2 targeting vector. Upper: The genomic structure surrounding the first coding exon (contains the start methionine codon) of Cat2. Center: The 5' and 3' homology regions of the targeting construct, the Neomycin (Neo) cassette and flanking herpes simplex virus thymidine kinase genes (HTK). Lower: The flanking probes and wxpected fragment sizes following restriction enzymes digests. Restriction sites indicated: S, SstI; H, HindIII; K, KpnI; E, EcoRI.
FIG. 22B shows the Southern blot analysis of ES cell genomic DNA with the 5' flanking probe.
FIG. 22C shows the Southern blot analysis of ES cell genomic DNA with the 3' flanking probe. Rearr.=chromosomal rearrangement.
FIG. 22D shows the Southern blot analysis of mouse genomic DNA using the 5' flanking probe.
Figure 23:
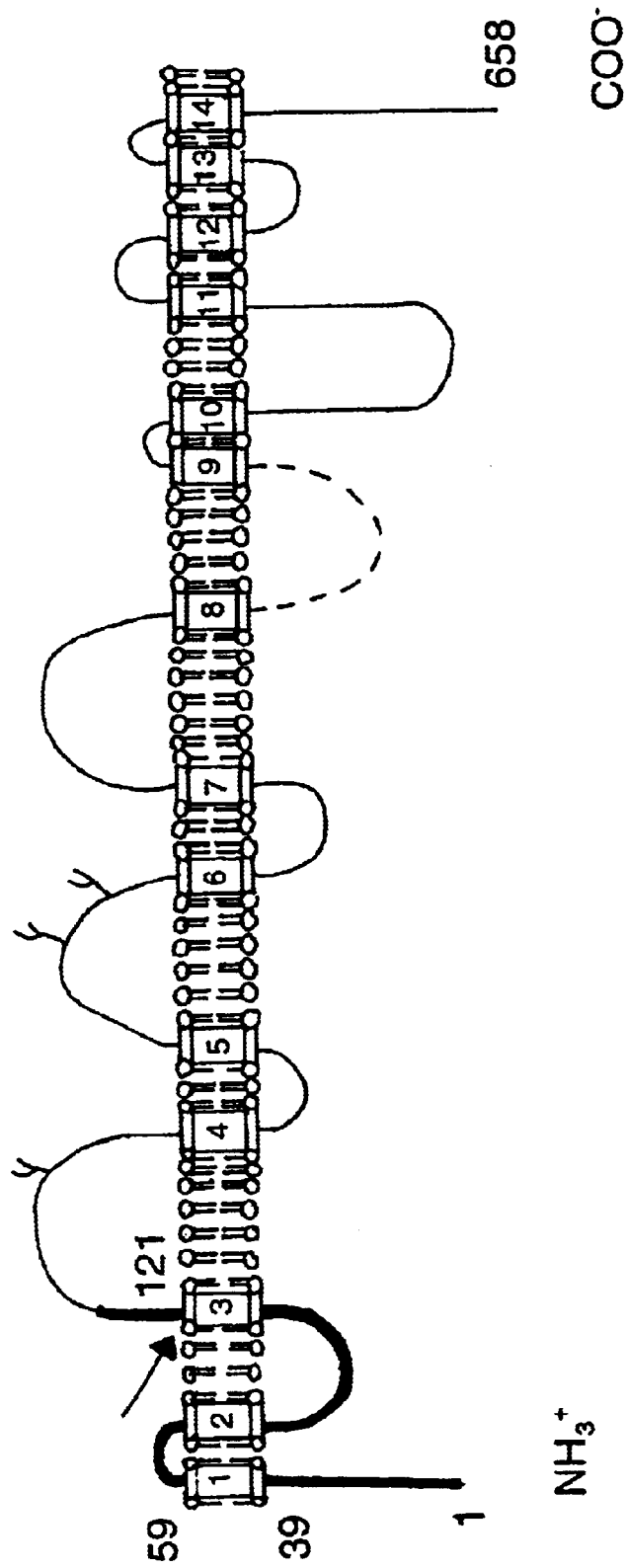

To determine whether CAT2 mediated arginine transport was required for NO production, the gene was disrupted by homologous recombination. The targeting vector for the Cat2 gene was constructed by replacing a 1.9 kb fragment including exon 2, the first coding exon of Cat2, with a 3.1 kb Neomycin cassette (FIG. 22A). It is the most highly conserved region of the protein. AB2.2 embryonic stem (ES) cells (Lexicon Genetics), transformed with the linearized targeting construct were selected in 180 µg/ml G418 and 200 nM 1(1-2-deoxy-2-fluoro-β-Darabinofuransyl)-5-iodouracil (FIAU) for 9 days. This is the classical "positive negative selection" pioneered by Mario Capecchi. The long regions of homology were used to increase the frequency of homologous recombination. Southern blotting of DNA from 384 drug resistant clones identified 7 containing the correct insert. Three diploid clones were injected into C57B1/6 blastocysts, all producing chimeric males (FIG. 22B, C). Only chimeras from one ES cell clone transmitted the mutant CAT2 allele to their progeny (FIG. 22D). The inbred Cat2$^{+/+}$, Cat2$^{2+/-}$ and Cat2$^{-/-}$ progeny were obtained in the predicted Mendelian ratios. Unlike Cat1$^{-/-}$ mice, Cat2$^{-/-}$ animals are completely viable, fertile, have no gross abnormalities providing evidence that Cat2 is a dispensable transporter gene (Perkins, et. al., *Genes Dev.*, 11: 914–925 (1997)).

Figure 24A:
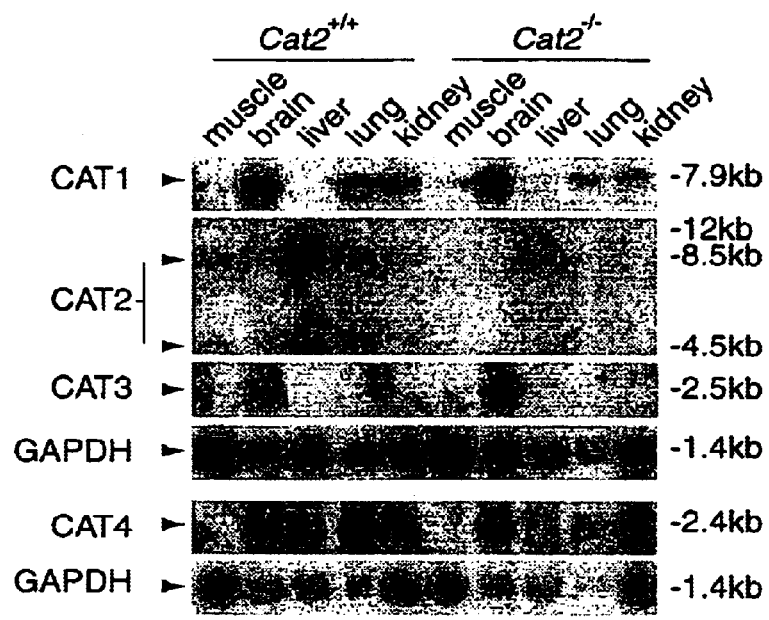
FIG. 24A shows a Northern blot analysis of RNA from the indicated $Cat2^{+/+}$ and $Cat2^{-/-}$ mouse tissues was probed sequentially with Cat1, Cat2, Cat3 and gapdh-specific cDNAs. A second membrane was probed with Cat4 gapdh-specific cDNAs. Nucleotide size markers (Life Technologies, Inc.) determined the relative size of each message. Wild type CAT2 cells express two transcripts (8.5 and 4.5 kb) that result from the use of alternate polyadenylation sites.
Figure 24B:
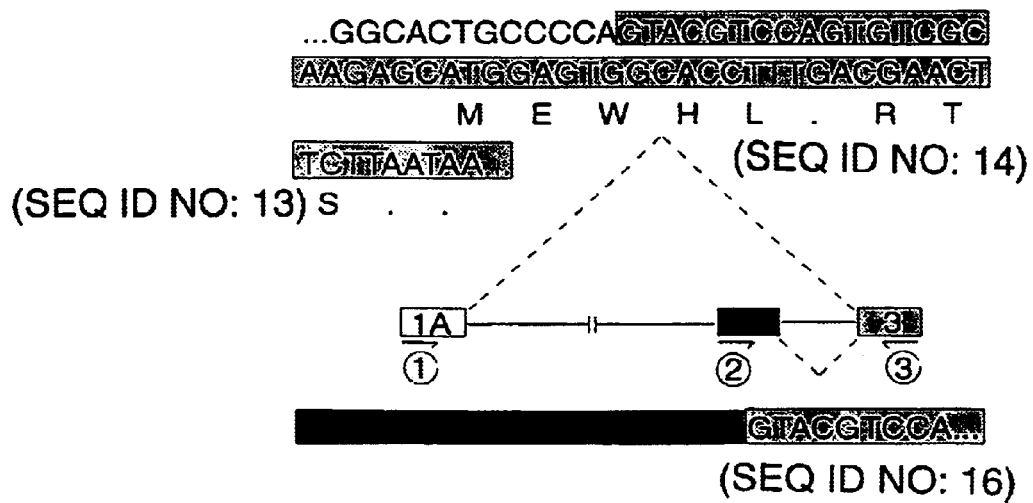
FIG. 24B shows DNA sequence analysis of RT/PCR products following amplification of truncated Cat2 mRNAs from $Cat2^{-/-}$ liver. Primers were specific for exon 1A and exon 3 or Neo and exon 3 as indicated. Also displayed are the predicted protein sequence and, in lower case letters, the non-coding sequence from the Neo targeting vector.

EXAMPLE 25
Amplification of Cat2$^{-/-}$ Transcripts from Cat2$^{-/-}$ Mouse Liver Cat2 transcripts from the liver of Cat2$^{-/-}$ mice were amplified by ART/PCR using oligonucleotides (1) 5'-TGTCTGCGCGGATCTGGAAAGG-3' (SEQ ID NO: 8) and (3) 5'-CGCGAATTCGTCTGGATACTCTGCCAG-3' (SEQ ID NO: 10) or (2) 5'-GCCCTGAATGAACTGCA-GGACG-3' (SEQ ID NO: 9) and (3) 5'-CGCGAATT-CGTCTGGATACTCTGCCAG-3' (SEQ ID NO: 10) (FIG. 24B). Following purification using QIAquick PCR purification (QIAGEN), automated DNA sequence analysis was performed using the dame oligonucleotide pairs as sequencing primers. RNA from mouse tissues and peritoneal macrophages was prepared with TRIzol (Life Technologies, Inc.). 10 µg of tissue or 5 µg of macrophage RNA were analyzed with Cat1, Cat2 and GAPDH. A 1.4 kb SstI fragment of hCat4, 1.3 kb BstXI/XhoI fragment of Cat3 were isolated for random-prime labeling. the NOS2 cDNA probe was cloned by RT/PCR from mouse mammary tumor cDNA using primers 5'-CAGTGCCCTGCTTTGTGC-GAAGT-3' (SEQ ID NO: 11) and 5'-AACGTTT-CTGGCTCTTGAGCTGGAA-3' (SEQ ID NO: 12) (FIG. 24A). The product was ligated into the vector pGEM-T Easy (Promega) and the sequence verified using flanking T7 and SP6 primers. Densitometry was performed probes (Nicholson, et al., *J. Biol. Chem.* 273: 14663–14666(1998)).

EXAMPLE 26
Lack of Expression of Compensatory CAT mRNA in Other Tissues in Cat2$^{-/-}$ Mice The expression of other CAT mRNA levels was tested to determine whether another family member increased expression to compensate for the functional loss of CAT2 transport. No compensatory increase in muscle, brain, liver, lung, or kidney was detectable in those tissues that constitutively express the Cat 2 gene. Inspection of the Northern blots, however, revealed detectable truncated CAT2 transcripts in the liver of Cat2$^{-/-}$ mice (FIG. 24A) that were 400 bp shorter than wild type 4.5 and 8.5 Kb mRNAs (see also FIG. 25B). The truncated transcripts from Cat2$^{-/-}$ liver were assessed in RT/PCR reactions to verify the absence of exon 2 using primers specific for (1) an upstream noncoding Cat2 liver promoter (exon 1A) or (2) the neomycin cassette, with (3) exon 3. DNA sequence analysis confirmed the absence of exon 2 and revealed the truncated transcripts initiated at either the promoter adjacent the noncoding exon 1A or within the Neo construct. These transcripts both spliced correctly into exon 3 (FIG. 24B). Since exon 1A is non-coding, any initiating methionine in the Cat2$^{-/-}$ transcripts must lie within or downstream of exon 3 (Finley, et al., *Proc. Natl. Acad. Sci. USA* 92: 9378–9382 (1995)). Inspection of the exon 3 DNA sequence disclosed the first long open reading frame is located +466 into the Cat2 coding sequence, constituting a loss of 24% of the CAT2 protein if the transcript were translated. The missing portion encodes the most conserved Cat sequences and includes a conserved glutamate residue essential for CAT1 function. This extensive loss makes it extremely unlikely that a functional CAT2 transporter was synthesized. (C. L. MacLeod, *Biochem. Soc. Transactions* 24: 846–852 (1996); Wang, et al., *Virology* 202: 1058–1060 (1994)).

EXAMPLE 27
Isolation and LPS/IFN-γ Stimulation of Peritoneal Macrophages

Inflammatory peritoneal macrophages (A. H. Fortier, in *Current Portocols in Immunology*, Coligan, et al., Ed. (John Wiley & Sons, New York, 1994) pp.14.1.1–14.13) were initially cultured 2 hrs, washed to remove unattached cells and, where indicated, primed with 20 U/ml IFN-γ for 2 hrs, 100 ng/ml LPS added and incubated 17 hours. Following activation, triplicate L-arg transport measurements were made in 400 µM L-arg probes (Nicholson, et al., *J. Biol. Chem.* 273: 14663–14666 (1998)). Additional triplicate uptake measurements were made 24 hrs following cytokine removal. The media was assessed for $NO_2^-$ and $NO_3^-$, the stable end products of NO metabolism (Verdon, et al., *Anal. Biochem.*, 224: 502–508 (1995)). Protein lysates were prepared from control and activated macrophages (Kakuda, et al., *Biochem. Biophys. Acta*, 1414: 75–84 (1998)). Lysates were concentrated usiang Centricon-309 concentrators (Amicon), the protein quantitated usin Bio-Rad DC and 20 µg of protein lysate was separated on 10% SDS-PAGE under reducing conditions. Western blots were incubated 2 hrs with 0.25 µg/ml polyclonal NOS2 antisera (Transduction Laboratories), washed repeatedly, incubated with 1:10,000 goat anti-rabbit horseradish peroxidase conjugate (Bio-Rad) and the protein detected by chemiluminescence (NEN Life Science Products). Macrophages were derived from mice of mixed C57B1/6-129 background except C57B1/6 Cat2$^{+/+}$ macrophages were used for data generated in FIGS. 25B, 25C, and 25D.

EXAMPLE 28

Figure 25A:
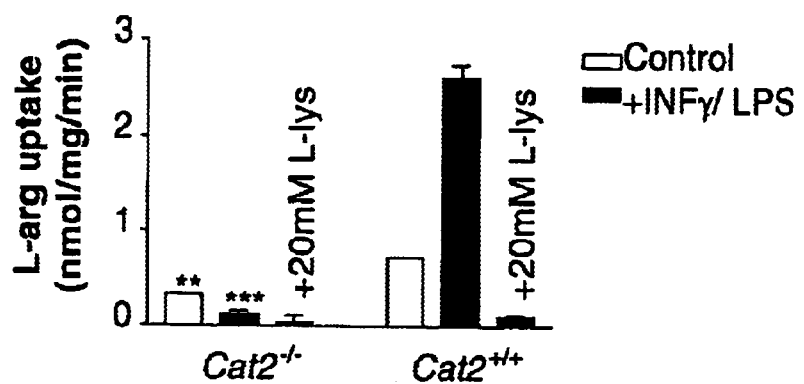
FIG. 25A shows L-arg uptake measured in $Cat2^{+/+}$ and $Cat2^{-/--}$ macrophages activated with INFγ and LPS with or without 20 mM L-lys as indicated (mean±S.E.M. of three determinations for each condition). , p<0.01 versus activated $Cat2^{---/-}$ macrophages; *, p<0.001 versus activated $Cat2^{+/+}$ macrophages.
Figure 25B:
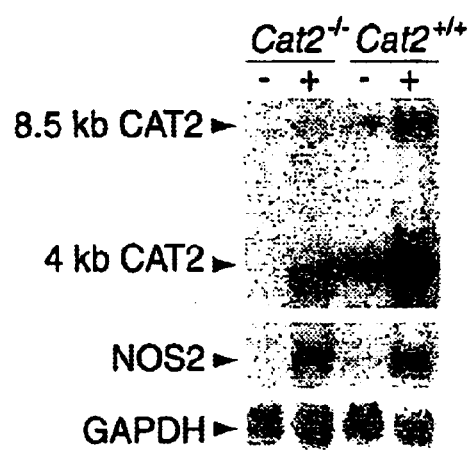
FIG. 25B shows a Northern blot analysis of RNA from control (−) and activated (+)Cat2$^{-/-}$ and Cat2$^{+/+}$ macrophages.
Figure 25C:
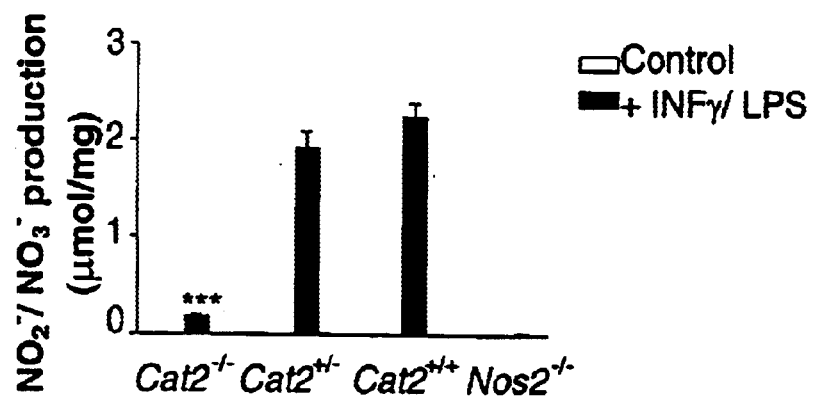
FIG. 25C shows nitrite and nitrate production of control and activated Cat2$^{-/-}$, Cat2$^{+/-}$, Cat2$^{+/+}$ and Nos2$^{-/-}$ macrophages (mean±S.E.M. of triplicate determinations). ***, p<0.001 versus activated Cat2$^{+/+}$ macrophages.

L-arginine Uptake and Nitric Oxide Production in Cat2$^{-/-}$ Macrophages Following LPS/IFN-γ Stimulation Once it was determined that the knockout mice fail to make CAT2 protein, it was necessary to determine whether macrophages from Cat2$^{-/-}$ mice had diminished system y+ transport activity. L-arginine uptake was measured in control and activated Cat2$^{+/+}$ and Cat2$^{-/-}$ peritoneal macrophages (A. H. Fortier, in *Current Portocols in Immunology*, Coligan, et al., Ed. (John Wiley & Sons, New York, 1994) pp.14.1.1–14.13). FIG. 25A shows that Cat2$^{-/-}$-derived macrophages are highly impaired in arginine uptake demonstrating that the Cat2$^{-/-}$ knockout was successful. The Cat2$^{-/-}$ activated macrophages were impaired in their capacity to take up arginine compared to wildtype cells. As expected, the initial rate of L-arg transport into wild type macrophages increased 3.6 fold following activation with Interferon γ and lipopolysaccharide. The uptake was competitively inhibited by L-lys, a system y+ substrate (White, et al., *J. Biol. Chem.* 257: 4443–4449 (1982)). System y+ mediated uptake of L-arg was significantly reduced in both Cat2$^{-/-}$ control and activated macrophages, providing strong evidence that CAT2 function was effectively ablated (Nicholson, et al., *J. Biol. Chem.* 273: 14663–14666 (1998)). The decrease in arginine uptake in activated Cat2$^{-/-}$ cells corresponds to the known decrease in Cat1 expression (Table 1) when macrophages (Kakuda, et al., *Biochem. Biophys. Acta.* 1414: 75–84 (1998); Sweet, et al., *J. Interferon Cytokine Res.* 18: 263–271 (1998)) and vascular smooth muscle cells (Gill, et al., *J. Biol. Chem.* 271: 11280–11283 (1996)) are activated. The observation that truncated CAT2 transcripts (FIG. 25B) were induced in activated Cat2$^{-/-}$ macrophages contemporaneous with a decrease in y+ transport activity further supports the conclusion that the Cat2 mutation is a null allele.

Figure 25D:
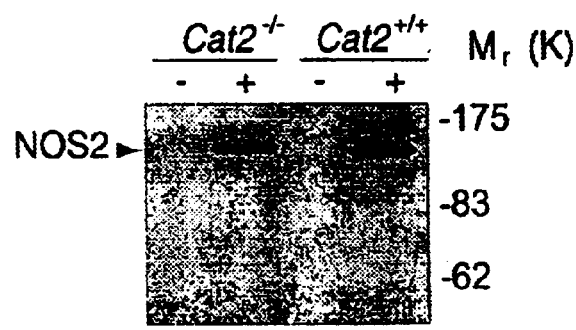
FIG. 25D shows a Western Blot analysis of NOS2 expression in coantrol(−) and activated (+) Cat2$^{-/-}$ and Cat2$^{+/+}$ macrophages. Protein size markers (New England BioLabs) are indicated. Each experiment was condicted at least twice with essentially identical results.

NOS2 transcripts increased following macrophage activation, although to a lesser extent in Cat2$^{-/-}$ cells (FIG. 25B) while NOS2 protein accumulated to a similar extent in cells of both genotyped (see FIG. 25D). Cat1 was not perceptible by Northern analysis, but was detected by RT/PCR in both Cat2$^{+/+}$ and Cat2$^{-/-}$ macrophages. Since CAT3 mRNA was not detected by RT/PCR, it appears that CAT1 protein accounts for the basal rate of system y+ transport acxtivity in Cat2$^{-/-}$ macrophages.

Production of NO (NO$_2^-$ and NO$_3^-$) by NOS2 was investigated in control and activated peritoneal macroophages isolated from Cat2$^{+/+}$, Cat2+/−, Cat2$^{-/-}$ and Nos2$^{-/-}$ mice (Laubach, et al., *Proc. Natl. Acad. Sci. USA* 92: 10688–10692 (1995)). Cytokine stimulated Cat2$^{-/-}$ macrophages made only 8% of the NO generated by wild type cells (FIG. 25C) but expressed similar amounts of NOS2 protein (FIG. 25D). NO synthesis in these cells was derived solely from NOS2 since neither NOS3 nor NOS1 were detected in either wild type or mutant cells. Cat2$^{+/-}$ and Cat2$^{+/+}$ macrophages produced comparable amounts of NO while macrophages from Nos2$^{-/-}$ mice failed to synthesize NO, as expected, following activation (FIG. 25C) (MacMicking, et al., *Annuu. Rev. Immunol.* 15: 323–350 (1997); (Laubach, et al., *Proc. Natl. Acad. Sci. USA* 92: 10688–10692 (1995)). Moreover, comparison of cytokine stimulated Cat2$^{-/-}$ and Cat2$^{+/+}$ enbryonic fibroblast cell lines and primary astroglial culatures also demonstrated a significant reduction in No synthesis in the mutant cells. The 94% reduction in system y+ transport together with a 92% reduction in NO production exhibited by Cat2 deficient activated macrophages provides strong genetic evidence that loss of CAT2 mediated L-arginine transport limits NO production in these cells. These cells represent crucial controls for high throughput assays to screen for drugs which block CAT2 transport. Clearly, there may be important and exploitable cell type differences in the requirement for CAT2 transport activity in nitric oxide production.

Figure 26:
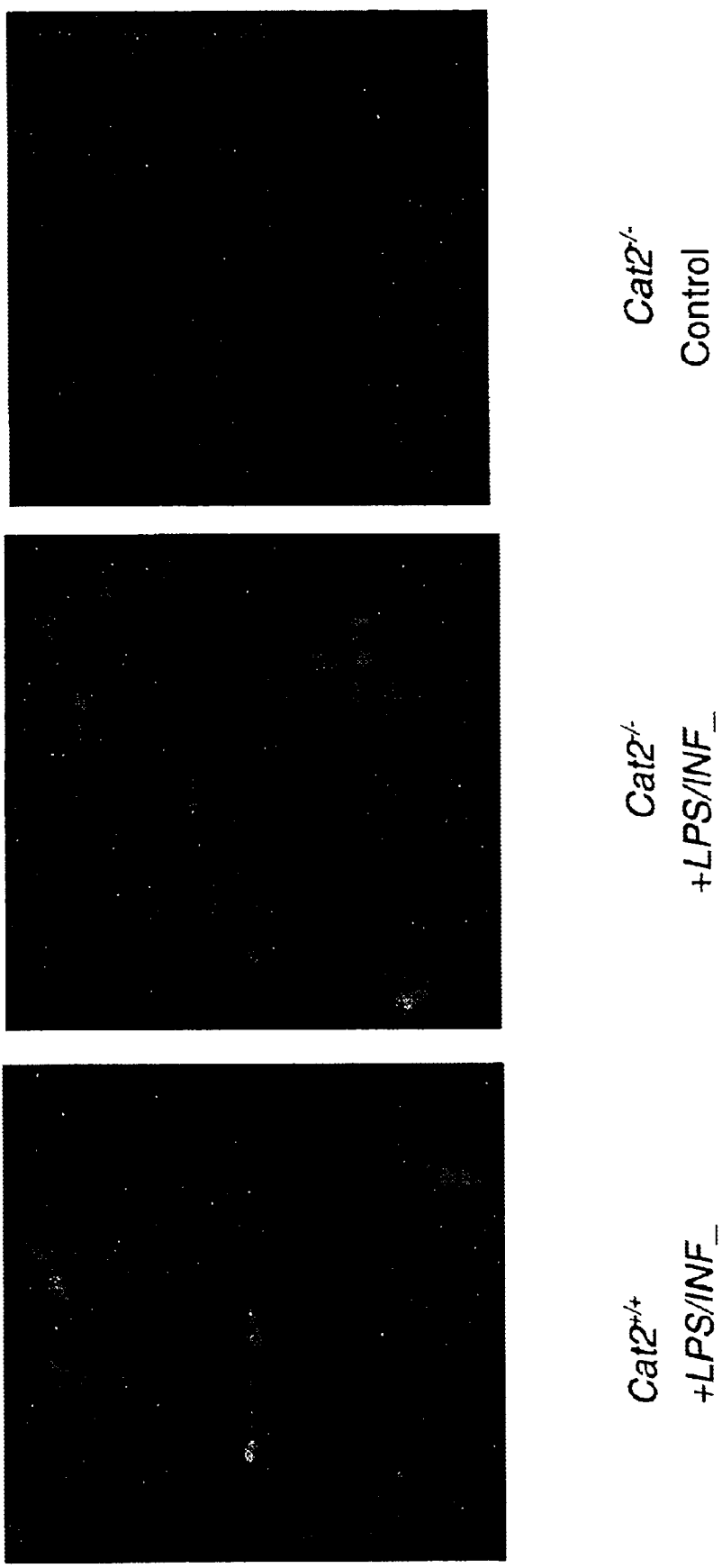
FIG. 26 shows that cytokine stimulation induces iNOS protein expression in CAT2$^{-/-}$ and CAT2$^{-+/+}$ macrophages. Cells of both genotypes synthesize detectable amounts of iNOS protein. Cells from both genotypes also fail to express this iNOS protein without cytokine activation, as illustrated in the CAT2$^{-/-}$ control panel.

Total body production of nitric oxide in different Cat2 genotypes was determined by collecting urine overnight from mice fasted for 6 hours. FIG. 26 shows that Cat2$^{-/-}$ mice produce about 50% the amount of nitric oxide produced by wild type or heterozygous littermates. Output of nitric oxide from iNos deficient mice is shown for comparison. The data show that Cat2$^{-/-}$ mice produce less nitric oxide than wild type but more than iNOS deficient mice. Hence, it seems likely that some nitric oxide production from iNOS does not require CAT2 transport function.

Cat2$^{-/-}$ mice cannot survive on an arginine free diet. In setting up the Cat2$^{-/-}$ mice on an arginine-free diet for the experiment shown in FIG. 27, it was noted that the mice gradually lose weight and succumb to starvation when maintained on the diet for more than a week. Their heterozygous and wild type littermates maintain their body weight and appear perfectly healthy on the same diet. The reason Cat2$^{-/-}$ mice fail to thrive on this diet is not known. One possibility is that CAT2 may mediate arginine efflux into plasma following glomerular filtration.

EXAMPLE 29

Antibody Production to CAT2

Figure 18:
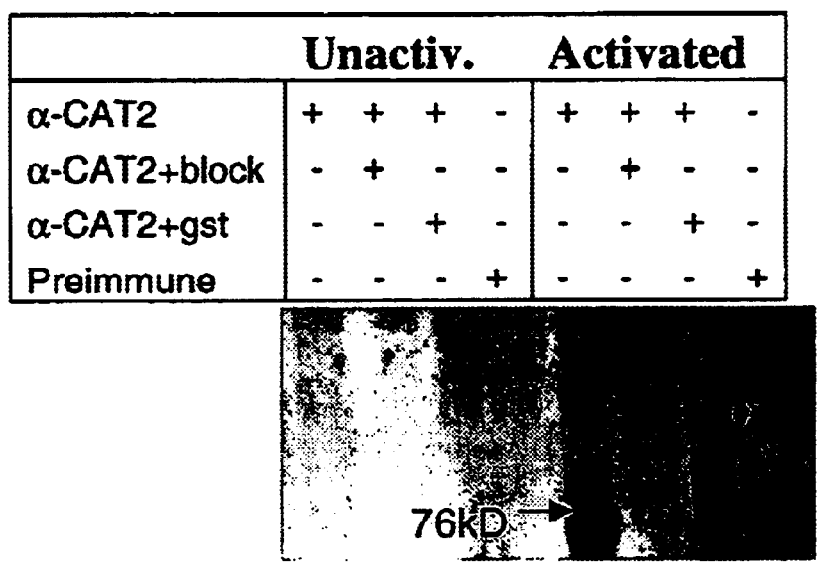
FIG. 18 shows the specificity of the anti-CAT2 antiserum. Peritoneal macrophages harvested from mice that had been previously injected with thioglycollate were subsequently cultured without (Unactiv.) or with IFN-γ and LPS (Activated) for 17 hours. Western blots of total cell lysates were cut into strips. They were separately reacted with antisera to the carboxy-terminus of CAT2 fused with glutathione-S-transferase ((Anti-CAT2), or blocked with either CAT2-GST fusion protein or with GST. Additional strips were reacted with the preimmune sera as noted. The CAT2 protein is glycosylated, resulting in fuzziness of the immunoreactive protein bands.
Figure 19:
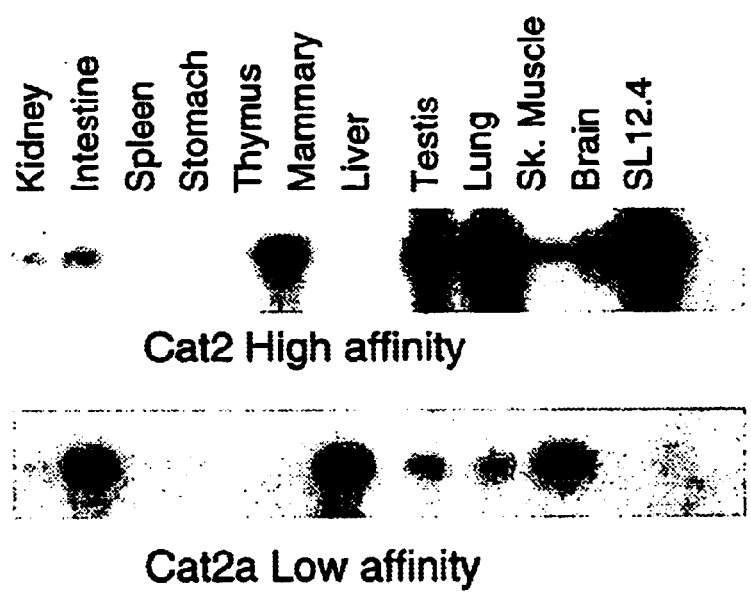
FIG. 19 illustrates CAT2/2a expression in various tissues. RNA from the indicated tissues was analyzed by Northern blotting and the filters probed with CAT2 and CAT2a specific oligonucleotides. The far right lane contains RNA from the SL12.4 cell line (T-lymphoma) from which CAT2 cDNA was cloned. A total of 15 other tissues were tested; none express CAT2 constitutively.
Figure 20:
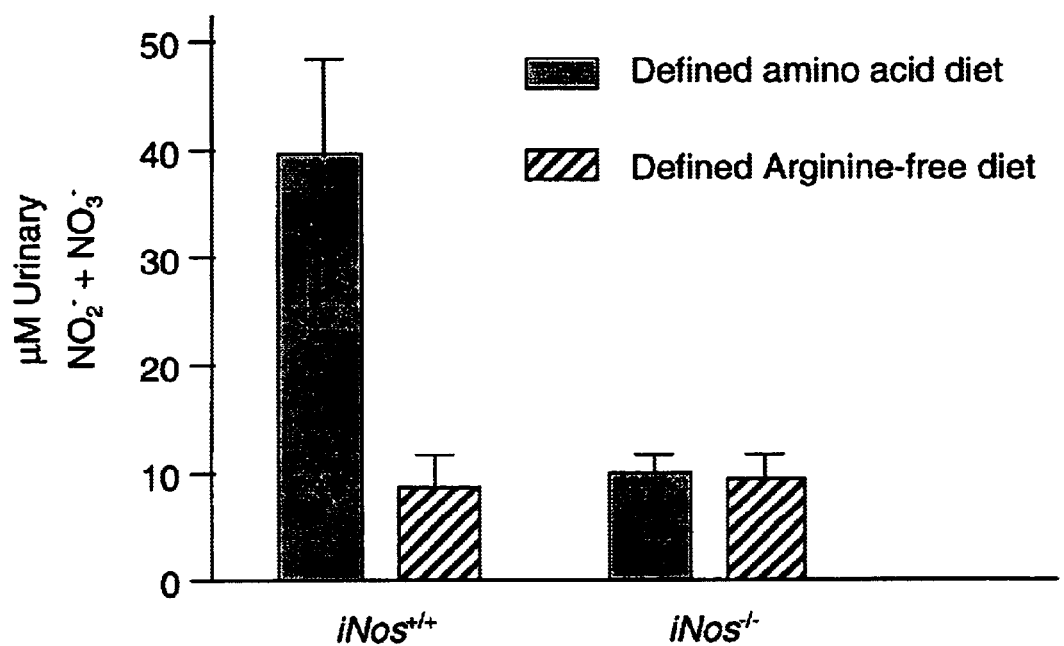
FIG. 20 shows that diet and iNos genotype change total body nitric oxide production. Urinary nitrite and nitrate were used to estimate total body production of nitric oxide following two weeks on defined diets that lack or have L-arginine. Urine was collected during a six-hour fasting period. The amount of nitric oxide produced by wild-type mice fed the defined arginine-free diet was essentially identical to that produced in the $iNos^{-/-}$ mice.
Figure 21:
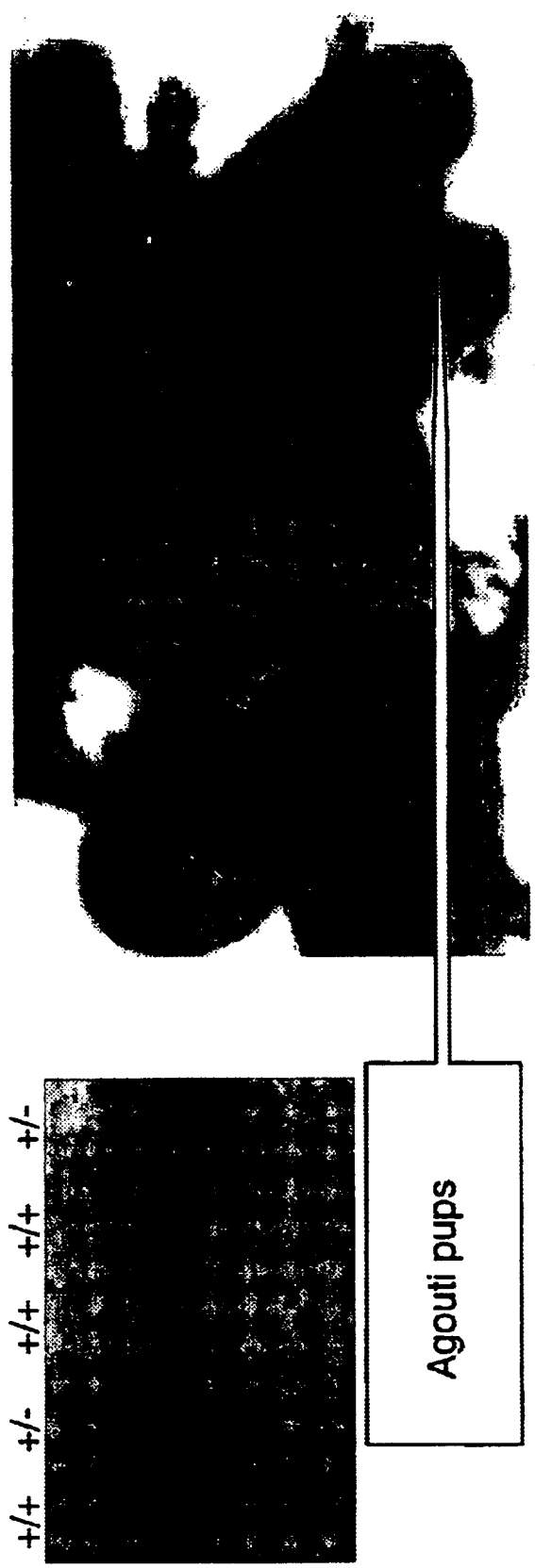
FIG. 21 shows the successful targeting of the CAT2 gene. The autoradiograph shows the disrupted allele in two ES clones. The restriction fragment from wild type mice is 11 kb; the presence of the targeted allele is demonstrated by a 7.5 kb fragment generated by the insertion of a new restriction site within the Neo construct used to disrupt the gene (arrowhead). The photo shows the agouti pups with their black mother. Agouti pups were genotyped to identify heterozygotes and mated to produce $CAT2^{-/-}$ homozygotes.

The production of antisera to all the CAT proteins has been exceedingly difficult. Only antisera directed to a fusion protein of GST and the COOH terminus region of CAT2 is reactive on Western blots and yields usable antisera against CAT2 protein from cells (FIG. 18).

EXAMPLE 30

Measurement of NO in Plasma and Urine

Production of total body nitric oxide in all of the experimental groups is assessed by plasma and urinary nitrate and nitrite determinations. In addition, plasma arginine is assessed from five mice in each group when they are six weeks of age. This is done by providing serum to the University of California at San Diego Clinical Laboratory. This test requires 150 ml of plasma and arginine is assessed by HPLC with orthophthaldialdehyde coupling and fluorimetric detection. Determination of circulating arginine levels is an important assay in further characterizing each genotype.

EXAMPLE 31

Mammary Gland Transplantation

Figure 27:
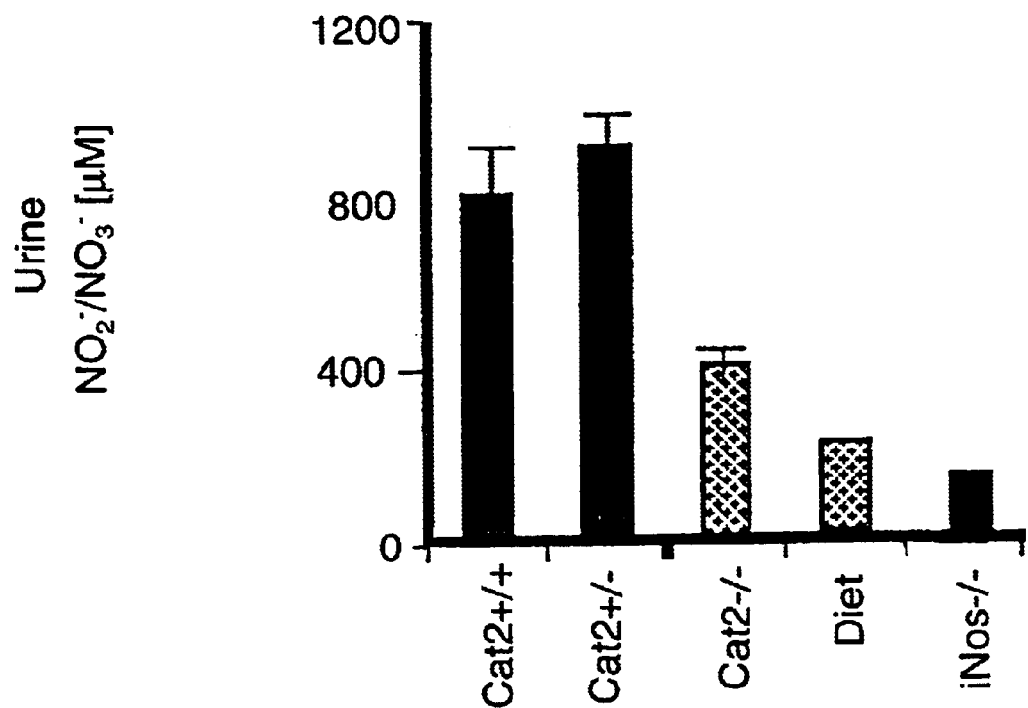
FIG. 27 demonstrates that CAT2 knockout mice produce 30–50% less nitric oxide than wild type mice. Urine was collected from mice of the indicated genotypes housed in metabolic cages for 24 hours. The data show that the CAT2 knockout mice produce less total nitric oxide and that production is further reduced by an arginine-free diet. Output of nitric oxide from iNOS deficient mice is shown for comparison.
Figure 28:
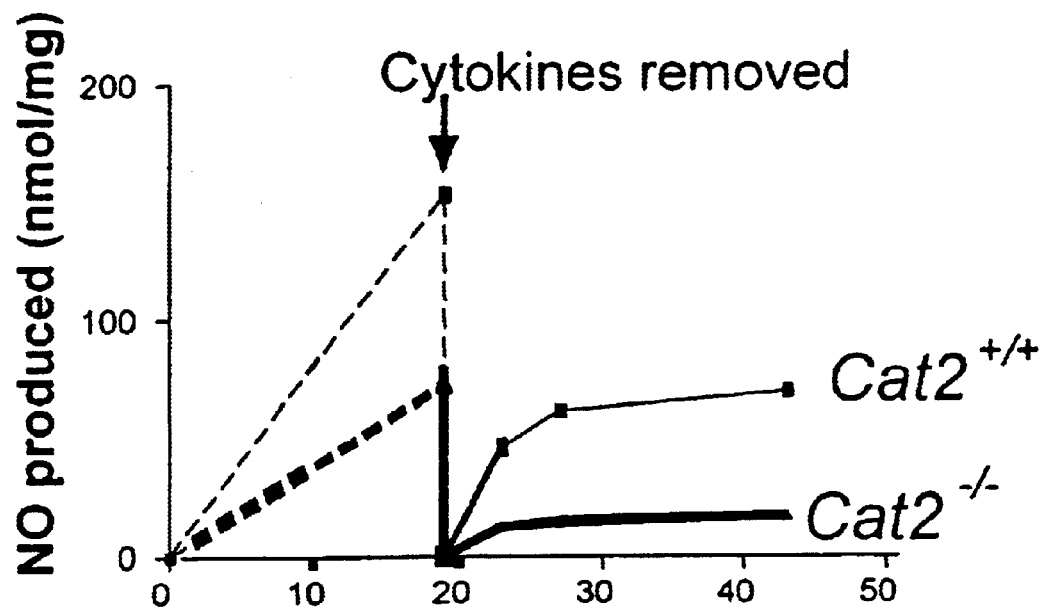
FIG. 28 demonstrates that Cat2$^{-/-}$ fibroblasts have reduced nitric oxide production. The cells were stimulated with a cocktail of IL1-β INF-γ and TNF-α or 20 hours, the cytokines removed and the cells incubated for the intervals shown. Nitrite and nitrate were measured by the Greiss to estimate the production of nitric oxide. The data were normalized to mgs of cellular protein. The lower heavy line shows nitric oxide production from the Cat2 deficient fibroblasts as indicated.

To address the cellular basis for iNOS and CAT2 modulation of mammary tumor progression, transplantation studies are essential. This will determine whether the mammary epithelial cells and/or the surrounding tissue are responsible for the differences in tumor progression seen in the various genotypes. Mammary epithelial cells from mTag mice of different ages and genotypes are transplanted into cleared mammary fat pads of recipients of various genotypes (iNos$^{+/+}$, iNos$^{-/-}$, Cat$^{-+/+}$, Cat2$^{-/-}$) as illustrated in FIG. 27. The recipients are then monitored for tumor growth and pulmonary metastasis, in order to ascertain whether NO acts by modifying the intrinsic growth properties of the mammary epithelial cells or by modulating their behavior via interactions with the mammary stroma, infiltrating macrophages or host vasculature, or a combination thereof.

As the juvenile mouse mammary gland matures, it undergoes extensive epithelial proliferation, leading to a network of ductal branching that transverses the organ. The epithelial cells of the mammary pad are confined to a small space and are easily removable at three weeks of age. Such removal of the epithelial cells is called "clearing the fat pad". To clear the #4 and #5 mammary pads, they are identified in anesthetized mice and a 1.5 cm midline incision is made between the #4 nipples. Angled lateral incisions are made from the midline point between the #4 nipples and ending at a point between the #4 and #5 nipples. The skin is loosened from the body wall, so to expose the #4 and #5 fat pads. The #4 nipple blood vessel and the blood vessel at a point on the fat pad bridge between are then cauterized. The triangular area defined by the cautery points are then excised, using iris scissors, and discarded. The developing mammary gland does not grow past the lymph node into the #4 mammary pads in 3 to 4 week old female mice. Removal of this region results in a "cleared" #4 mammary fat pad into which tissues can be transplanted without interference from the host's mammary gland.

The donor animal undergoes a similar procedure at 8 weeks of age. 1–2 mm$^3$ of mammary epithelial cells are used. A pocket in the middle of the fat pad is used for tissue implantation. The pocket is prepared by holding points of jeweler's forceps together and inserting the points into the fat pad such that they do not rupture the surrounding connective tissue layer on the underside.

EXAMPLE 32
Analysis of Arginine Transport and NO Production

Cell lines from mTag transgenic mammary adenocarcinoma tumors have been established. The capacity of the iNos$^{+/+}$, iNos$^{-/-}$ derived mammary adenocarcinoma cell lines to transport L-arginine can be determined using $^3$H-labeled L-arginine and lysine in a manner identical to that of Example 2. The effect of altering the L-arginine conditions in the media, e.g. low concentration of ca. 50 $\mu$M, regular 200 $\mu$M and high 1 mM—can be ascertained. Further, these cells can be stimulated with cytokine cocktails while cultured in these media to examine the coordinate induction of iNOS and CAT2 proteins in mTag iNos$^{+/+}$ and Cat2$^{-/-}$ cells.

The production of NO can be examined by detecting the stable products nitrite and nitrate via the Greiss reagent from cell supernatants. Cell lines from the iNos$^{-/-}$ mice permit the measurement of the eNOS and nNos contribution to NO production in mammary cell adenocarcinomas. The relative levels of CAT1, CAT2, CAT3 and NOS protein in cell lines from each genotype can be easily assessed by immunodetection e.g. Western blotting and immunocytochemistry. Expression of mRNA can be determined by such methods as RT-PCR and Northern blotting. Such assessments provide a basis for further investigation of the possible interaction of iNOS and CAT proteins.

EXAMPLE 33
Analysis of CAT2/iNOS Protein Interactions

A GST-CAT2 fusion protein binds to radiolabeled pure iNOS in a specific fashion. This demonstrates that CAT2 and iNOS interact directly and tightly. Additionally, this interaction can be explored using the yeast two-hybrid system. This can determine interactions of iNOS with each of the eight predicted intracellular domains of CAT2, giving more information regarding topology of the protein.

EXAMPLE 34
Microsatellite Instability Analysis

The frequency of the 'mutator phenotype' in mammary tumors can be investigated as a possible target for nitric oxide mutagenesis. In such an assessment, DNA extracted from tumors and normal liver tissue is subjected to PCR. Four end-labeled primer pairs are used to amplify sequences containing dinucleotide repeats; four other pairs are used to amplify sequences containing mononucleotide repeats (e.g. Edelman, et al., Cell, 91:467–477, 1997). Amplified products are separated on a denaturing polyacrylamide gel. Extent of microsatellite instability is compared from cell lines to determine whether they are different from primary tumors in this respect.

Because there is a high degree of correlation between the presence of germline mutations in Msh2 and Mlh1 genes and the extent of microsatellite instability, the expression of these proteins is also examined via immunohistochemistry in both the tumor samples and the cell lines. When these proteins are down-regulated or mutated, their expression is frequently diminished.

The immunohistochemistry protocol for these proteins has been described (Kane, M., et al., Cancer Research, 57:808–811 (1997)). Briefly, 5 $\mu$m sections are deparaffinized and re-hydrated in graded alcohols. The sections are then washed and subjected to antigen retrieval by microwave irradiation with antigen retrieval solution. Following this, the sections are incubated with monoclonal anti-Mlh1 or anti-Msh-2 antibodies (Oncogene Science) followed by a post-treatment using glutaraldehyde fixative. Normal tissue adjacent to the tumor is used as a control.

EXAMPLE 35
p53 Expression and Mutational Analysis

As described supra, the status of the p53 gene and its expression and localization are important in the progression of tumors. Hence, it is of interest to examine the expression of p53 by immunohistochemistry, RT/PCR and sequence analysis. The sequence of p53 is determined in 20 tumors of each genotype by directly sequencing RT/PCR products. Sequencing is done on an ABI Sequenator using primers within the coding sequence of p53. Immunostaining is carried out using a commercially available antibody (Oncogene Science). This analysis can help determine whether NO status has an effect on p53 function.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inhibiting cationic amino acid transport comprising the step of administering to a human or a non-human mammal an effective dose of an antisense oligonucleotide directed against CAT2 mRNA.

2. The method of claim 1, wherein said antisense oligonucleotide has the nucleotide sequence: GTAGGCTGAAACCCTGTCCTTGC (SEQID No. 2).

3. A method of inhibiting the production of nitric oxide in an individual in need of such treatment comprising the step of administering to said individual an effective dose of a pharmaceutical composition comprising an antisense oligonucleotide directed against CAT2 mRNA and a physiologically acceptable carrier.

4. A method of treating a pathophysiological state in an individual wherein said state is characterized by production of an undesirable level of nitric oxide, comprising the step of administering to said individual an effective dose of a pharmaceutical composition comprising an antisense oligonucleotide directed against CAT2 mRNA and a physiologically acceptable carrier.

5. The method of claim 4, wherein said pathophysiological state is selected from the group consisting of sepsis, neoplastic disease, autoimmune diseases, cachexia, cerebral malaria, cardiovascular disease, cerebrovascular disease and capillary leak syndrome.

6. The method of claim 5, wherein said autoimmune disease is selected from the group consisting of systemic lupus erythematosus, rheumatoid arthritis and multiple sclerosis.

7. The method of claim 5 wherein said neoplastic disease is selected from the group consisting of breast cancer and lung cancer.

8. A method of treating breast cancer in an individual in need of such treatment, comprising the step of administering to said individual an effective dose of a pharmaceutical composition comprising an antisense oligonucleotide directed against CAT2 mRNA and a physiologically acceptable carrier.

9. The method of claim 3, wherein said antisense oligonucleotide has the nucleotide sequence: GTAGGCTGAAACCCTGTCCTTGC (SEQ ID No. 2).

10. The method of claim 4, wherein said antisense oligonucleotide has the nucleotide sequence: GTAGGCTGAAACCCTGTCCTTGC (SEQ ID No. 2).

11. The method of claim 8, wherein said antisense oligonucleotide has the nucleotide sequence: GTAGGCTGAAACCCTGTCCTTGC (SEQ ID No. 2).

* * * * *